US011410440B2

(12) United States Patent
Skala et al.

(10) Patent No.: US 11,410,440 B2
(45) Date of Patent: Aug. 9, 2022

(54) SYSTEMS AND METHODS FOR CLASSIFYING ACTIVATED T CELLS

(71) Applicant: Wisconsin Alumni Research Foundation, Madison, WI (US)

(72) Inventors: Melissa C. Skala, Middleton, WI (US); Anthony Gitter, Madison, WI (US); Zijie Wang, Madison, WI (US); Alexandra J. Walsh, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 89 days.

(21) Appl. No.: 16/992,539

(22) Filed: Aug. 13, 2020

(65) Prior Publication Data

US 2021/0049346 A1  Feb. 18, 2021

Related U.S. Application Data

(60) Provisional application No. 62/886,139, filed on Aug. 13, 2019.

(51) Int. Cl.
*G06V 20/69* (2022.01)
*C12N 5/0783* (2010.01)
(Continued)

(52) U.S. Cl.
CPC ......... *G06V 20/698* (2022.01); *C12N 5/0636* (2013.01); *G06K 9/6257* (2013.01);
(Continued)

(58) Field of Classification Search
CPC .. G06V 20/698; G06V 10/454; G06V 20/695; C12N 5/0636; G06K 9/6257; G06K 9/6263; G06K 9/6271
See application file for complete search history.

(56) References Cited

U.S. PATENT DOCUMENTS

2014/0152801 A1* 6/2014 Fine ..................... H04N 7/18
348/79

OTHER PUBLICATIONS

Overbeeke et al, "Quantitative flow cytometry shows activation of the TNF-a system but not of the IL-2 system at the single cell level in renal replacement therapy" (published in Nephrology Dialysis Transplantation, vol. 16, Issue 7, Jul. 2001, pp. 1430-1435) (Year: 2001).*

(Continued)

*Primary Examiner* — Casey L Kretzer
(74) *Attorney, Agent, or Firm* — Quarles & Brady, LLP

(57) ABSTRACT

Systems and methods for classifying and/or sorting T cells by activation state are disclosed. The system includes a cell classifying pathway, a single-cell autofluorescence image sensor, a processor, and a non-transitory computer-readable memory. The memory is accessible to the processor and has stored thereon a trained convolutional neural network and instructions. The instructions, when executed by the processor, cause the processor to: a) receive the autofluorescence intensity image; b) optionally pre-process the autofluorescence intensity image to produce an adjusted autofluorescence intensity image; c) input the autofluorescence intensity image or the adjusted autofluorescence intensity image into the trained convolutional neural network to produce an activation prediction for the T cell.

20 Claims, 12 Drawing Sheets
(9 of 12 Drawing Sheet(s) Filed in Color)

(51) Int. Cl.
  *G06K 9/62* (2022.01)
  *G06V 10/44* (2022.01)
(52) U.S. Cl.
  CPC ......... *G06K 9/6263* (2013.01); *G06K 9/6271* (2013.01); *G06V 10/454* (2022.01); *G06V 20/695* (2022.01)

(56) References Cited

OTHER PUBLICATIONS

Simonyan, K., et al. Deep Inside Convolutional Networks: Visualising Image Classification Models and Saliency Maps. arXiv:1312.6034 [cs] (2013).
Springenberg, J. T., et al. Striving for Simplicity: The All Convolutional Net; arXiv:1412.6806 [cs] (2014).
Szegedy, C., et al. Rethinking the Inception Architecture for Computer Vision. arXiv:1512.00567 [cs] (2015).
Szulczewski, J. M. et al. In Vivo Visualization of Stromal Macrophages via label-free FLIM-based metabolite imaging. Sci. Reports 6 (2016).
Thomas, K. et al. Jupyter Notebooks—a publishing format for reproducible computational workflows. Stand Alone 87-90 (2016).
Varma, S. et al. Bias in error estimation when using cross-validation for model selection. BMC Bioinforma. 7, 91 (2006).
Walsh, A. et al. Label-free Method for Classification of T cell Activation. bioRxiv (2019).
Wang, X. et al. ChestX-Ray8: Hospital-Scale Chest X-Ray Database and Benchmarks on Weakly-Supervised Classification and Localization of Common Thorax Diseases. In 2017 IEEE Conference on Computer Vision and Pattern Recognition (CVPR), 3462-3471 (IEEE, Honolulu, HI, 2017).
Wang, Z.J et al. Classifying T Cell Activity with Convolutional Neural Networks. Poster presented at Great Lakes Bioinformatics Conference. May 19-22, 2019. Madison, WI.
Weigert, M. et al. Content-Aware Image Restoration: Pushing the Limits of Fluorescence Microscopy. bioRxiv (2018).
Yoon, J. et al. Identification of non-activated lymphocytes using three-dimensional refractive index tomography and machine learning. Sci. Reports 7, 6654 (2017).
Abadi, M. et al. TensorFlow: Large-Scale Machine Learning on Heterogeneous Systems (2015).
Abramoff, M. D. et al. Improved Automated Detection of Diabetic Retinopathy on a Publicly Available Dataset Through Integration of Deep Learning. Investig. Opthalmology & Vis. Sci. 57, 5200 (2016).
Adebayo, J. et al. Sanity Checks for Saliency Maps. In Bengio, S. et al. (eds.) Advances in Neural Information Processing Systems 31, 9505-9515 (Curran Associates, Inc., 2018).
Bannon, D. et al. DeepCell 2.0: Automated cloud deployment of deep learning models for large-scale cellular image analysis. bioRxiv (2018).
Bradski, G. The OpenCV Library. Dr. Dobb's J. Softw. Tools (2000).
Buggenthin, F. et al. Prospective identification of hematopoietic lineage choice by deep learning. Nat. Methods 14, 403-406 (2017).
Carpenter, A. E. et al. CellProfiler: image analysis software for identifying and quantifying cell phenotypes. Genome Biol. 7, R100 (2006).
Cazaux, M. et al. Single-cell imaging of CAR T cell activity in vivo reveals extensive functional and anatomical heterogeneity. J. Exp. Medicine (2019).
Chen, C. L. et al. Deep Learning in Label-free Cell Classification. Sci. Reports 6 (2016).
Ching, T. et al. Opportunities and obstacles for deep learning in biology and medicine. J. The Royal Soc. Interface 15, 20170387 (2018).
Chollet, F. & others. Keras (2015).
Deng, J. et al. ImageNet: A Large-Scale Hierarchical Image Database. In CVPR09 (2009).

Doan, M. et al. Leveraging machine vision in cell-based diagnostics to do more with less. Nat. Mater. 18, 414-418 (2019).
Durr, O. et al. Single-Cell Phenotype Classification Using Deep Convolutional Neural Networks. J. Biomol. Screen. 21, 998-1003 (2016).
Eulenberg, P. et al. Reconstructing cell cycle and disease progression using deep learning. Nat. Commun. 8, 463 (2017).
Falk, T. et al. U-Net: deep learning for cell counting, detection, and morphometry. Nat. Methods 16, 67-70 (2019).
Gavgiotaki, E. et al. Detection of the T cell activation state using nonlinear optical microscopy. J. Biophotonics 12, e201800277 (2019).
Godinez, W. J., et al. A multi-scale convolutional neural network for phenotyping high-content cellular images. Bioinformatics 33, 2010-2019 (2017).
Guo, B. et al., "High-throughput, label-free, single-cell, microalgal lipid screening by machine-learningequipped optofluidic time-stretch quantitative phase microscopy," Cytometry A 91, 494-502 (2017).
Guo, C., et al. On Calibration of Modern Neural Networks. arXiv:1706.04599 [cs] (2017).
Gupta, A. et al. Deep Learning in Image Cytometry: A Review. Cytom. Part A 95, 366-380 (2019).
Habibzadeh M. et al. Automatic white blood cell classification using pre-trained deep learning models: ResNet and Inception. In Zhou, J., Radeva, P., Nikolaev, D. & Verikas, A. (eds.) Tenth International Conference on Machine Vision (ICMV 2017), 105 (SPIE, Vienna, Austria, 2018).
Heo, Y. J., et al. Real-time Image Processing for Microscopy-based Label-free Imaging Flow Cytometry in a Microfluidic Chip. Sci. Reports 7, 11651 (2017).
Kandaswamy, C., et al. High-Content Analysis of Breast Cancer Using Single-Cell Deep Transfer Learning. J. Biomol. Screen. 21, 252-259 (2016).
Karandikar, S. H. et al. Reagent-Free and Rapid Assessment of T Cell Activation State Using Diffraction Phase Microscopy and Deep Learning. Anal. Chem. 91, 3405-3411 (2019).
Kensert, A., et al. Transfer Learning with Deep Convolutional Neural Networks for Classifying Cellular Morphological Changes. SLAS Discovery: Adv. Life Sci. R&D 24, 466-475 (2019).
Kraus, O. Z., et al. Classifying and segmenting microscopy images with deep multiple instance learning. Bioinformatics 32, i52-i59 (2016).
Lecun, Y., et al. Gradient-based learning applied to document recognition. Proc. IEEE 86, 2278-2324 (1998).
Lever, J., et al. Points of Significance: Classification evaluation. Nat. Methods 13, 603-604 (2016).
Lippeveld, M. et al. Classification of human white blood cells using machine learning for stain-free imaging flow cytometry. bioRxiv 680975 (2019).
Maaten, L. v. d et al. Visualizing data using t-SNE. J. Mach. Learn. Res. 9, 2579-2605 (2008).
Marek-Trzonkowska, N. et al. Administration of CD4+CD25highCD127-Regulatory T Cells Preserves Beta-Cell Function in Type 1 Diabetes in Children. Diabetes Care 35, 1817-1820 (2012).
McInnes, L., et al. UMAP: Uniform Manifold Approximation and Projection for Dimension Reduction. arXiv:1802.03426 [cs, stat] (2018).
McInnes, L., et al. UMAP: Uniform Manifold Approximation and Projection. J. Open Source Softw. 3, 861 (2018).
Moen, E. et al. Deep learning for cellular image analysis. Nat. Methods 1 (2019).
Nassar, M. et al. Label-Free Identification of White Blood Cells Using Machine Learning. Cytom. Part A (2019).
Nitta, N. et al. Intelligent Image-Activated Cell Sorting. Cell 175, 266-276.e13 (2018).
Pardoll, D. M. The blockade of immune checkpoints in cancer immunotherapy. Nat. Rev. Cancer 12, 252-264 (2012).
Parnamaa, T. et al. Accurate Classification of Protein Subcellular Localization from High-Throughput Microscopy Images Using Deep Learning. G3: Genes, Genomes, Genet. 7, 1385-1392 (2017).

(56) References Cited

OTHER PUBLICATIONS

Pavillon, N., et al. Noninvasive detection of macrophage activation with single-cell resolution through machine learning. Proc. Natl. Acad. Sci. 115, E2676-E2685 (2018).
Pawlowski, N., et al. Automating Morphological Profiling with Generic Deep Convolutional Networks. bioRxiv (2016).
Pearce, E. L. Metabolism in T cell activation and differentiation. Curr. Opin. Immunol. 22, 314-320 (2010).
Pedregosa, F. et al. Scikit-learn: Machine Learning in Python. J. Mach. Learn. Res. 12, 2825-2830 (2011).
Phan, H. T. H., et al. Transfer learning of a convolutional neural network for HEp-2 cell image classification. In 2016 IEEE 13th International Symposium on Biomedical Imaging (ISBI), 1208-1211 (IEEE, Prague, Czech Republic, 2016).
Project Jupyter et al. Binder 2.0—Reproducible, interactive, sharable environments for science at scale. Proc. 17th Python Sci. Conf. 113-120 (2018).
Raghu, M., et al. Transfusion: Understanding Transfer Learning for Medical Imaging. arXiv:1902.07208 [cs, stat] (2019).
Ramey, N. A., et al. Imaging Mitochondria in Living Corneal Endothelial Cells Using Autofluorescence Microscopy. Photochem. Photobiol. 83, 1325-1329 (2007).
Raschka, S. Model Evaluation, Model Selection, and Algorithm Selection in Machine Learning. arXiv:1811.12808 [cs, stat] (2018).
Restifo, N. P., et al. Adoptive immunotherapy for cancer: harnessing the T cell response. Nat. Rev. Immunol. 12, 269-281 (2012).
Shields et al., "Microfluidic cell sorting: a review of the advances in the separation of cells from debulking to rare cell isolation," Lab Chip, Mar. 7, 2015; 15(5): 1230-49.

\* cited by examiner

SYSTEMS AND METHODS FOR CLASSIFYING ACTIVATED T CELLS

CROSS-REFERENCE TO RELATED APPLICATIONS

This application is related to, claims priority to, and incorporated herein by reference for all purposes U.S. Provisional Patent Application No. 62/886,139, filed Aug. 13, 2019.

STATEMENT REGARDING FEDERALLY FUNDED RESEARCH

This invention was made with government support under CA205101 awarded by the National Institutes of Health. The government has certain rights in the invention.

BACKGROUND

One new cancer treatment being studied is CAR T cell (Chimeric Antigen Receptor T cell) therapy. CAR T cell therapy uses a patient's own cells and "re-engineers" them to fight cancer. It is a very complex treatment. Collecting and altering the cells is difficult, and CAR T cell therapy often causes very severe side effects. At this time, it is only offered at a few major cancer centers. To date, most of the patients treated with CAR T cells have been people with blood cancers.

The procedure starts with removing the patient's own T cells from their blood and sending them to a lab where they are altered to produce proteins called chimeric antigen receptors (CARs) on the surface of the cells. These special receptors allow the T cells to help identify and attack cancer cells. The "super-charged" T cells are multiplied and grown at the lab, then frozen and shipped back to the Hospital, where they re-inject these treated CAR T cells back into the patient's blood.

Current methods to determine T cell activation include flow cytometry, immunofluorescence imaging, and immunohistochemistry but these methods require contrast agents and may require tissue or cell fixation. A need exists for systems and methods for classifying and/or sorting T cells by activation state in a fashion that allows the sorted T cells to be used in subsequent procedures, such as CAR T cell therapy.

SUMMARY

In an aspect, the present disclosure provides a T cell classifying and/or sorting device. The device includes a cell analysis pathway, a single-cell autofluorescence image sensor, a processor, and a non-transitory computer-readable medium. The cell analysis pathway includes an inlet, an observation zone, and outlet, and an optional cell sorter. The observation zone is coupled to the inlet downstream of the inlet and to the outlet upstream of the outlet. The observation zone is configured to present T cells for individual autofluorescence interrogation. The optional cell sorter has a sorter inlet and at least two sorter outlets. The optional cell sorter is coupled to the observation zone via the sorter inlet downstream of the observation zone. The optional cell sorter is configured to selectively direct a cell from the sorter inlet to one of the at least two sorter outlets based on a sorter signal. The single-cell autofluorescence image sensor is configured to acquire an autofluorescence intensity image of a T cell positioned in the observation zone. The processor is in electronic communication with the single-cell autofluorescence image sensor. The non-transitory computer-readable medium is accessible to the processor. The non-transitory computer-readable medium has stored thereon a trained convolutional neural network and instruction. The instruction, when executed by the processor, cause the processor to: a) receive the autofluorescence intensity image; b) optionally pre-process the autofluorescence intensity image to produce an adjusted autofluorescence intensity image; c) input the autofluorescence intensity image or the adjusted autofluorescence intensity image into the trained convolutional neural network to produce an activation prediction for the T cell.

In another aspect, the present disclosure provides a method of characterizing T cell activation state. The method includes: a) optionally receiving a population of T cells having unknown activation status; b) acquiring an autofluorescence intensity image for a T cell of the population of T cells; c) optionally pre-processing the autofluorescence intensity image to provide an adjusted autofluorescence intensity image; and d) identifying an activation status of the T cell based on an activation prediction, wherein the activation prediction is computed using the autofluorescence intensity image or the adjusted autofluorescence intensity image as an input for a trained convolutional neural network.

In a further aspect, the present disclosure provides a method of sorting and/or classifying T cells. The method includes: a) receiving a population of T cells having unknown activation status; b) acquiring an autofluorescence intensity image for each T cell of the population of T cells, thereby resulting in a set of autofluorescence intensity images; c) optionally pre-processing the autofluorescence intensity images of the set of autofluorescence intensity images to provide a set of adjusted autofluorescence intensity images; and either: d1) physically isolating a first portion of the population of T cells from a second portion of the population of T cells based on an activation prediction, wherein each T cell of the population of T cells is placed into the first portion when the activation prediction exceeds a predetermined threshold and into the second portion when the activation prediction is less than or equal to the predetermined threshold; or d2) generating a report including the activation prediction, the report optionally identifying a proportion of the population of T cells having the activation prediction that exceeds the predetermined threshold. The activation prediction is computed using the autofluorescence intensity image from the set of autofluorescence intensity images or the adjusted autofluorescence intensity image from the set of adjusted autofluorescence intensity images corresponding to a given T cell as an input for a trained convolutional neural network.

In yet another aspect, the present disclosure provides a method of administering activated T cells to a subject in need thereof. The method includes: a) the method of sorting and/or classifying T cells as described herein; and b) introducing the first portion (or any portion including a sufficient amount of activated T cells) to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
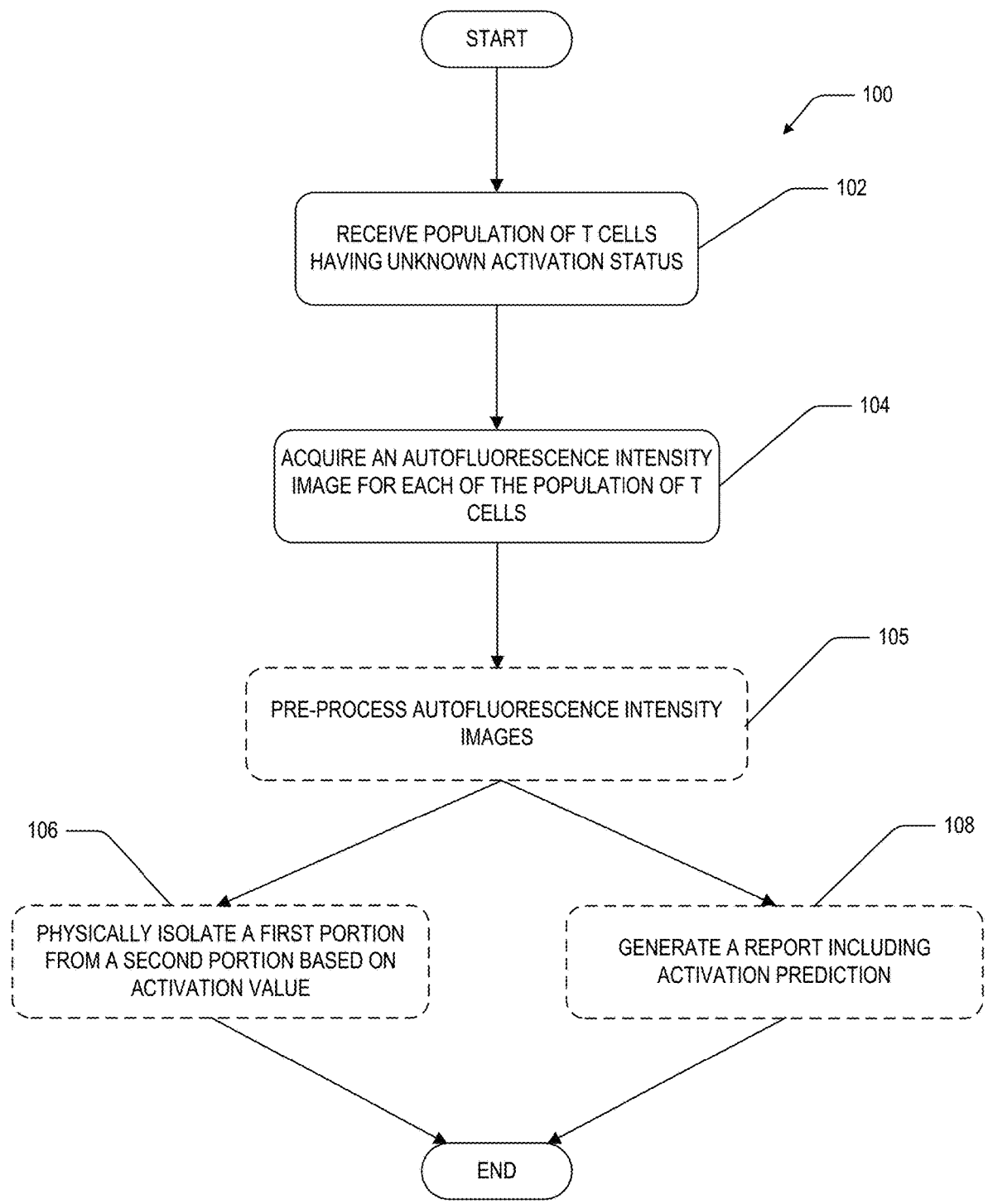
FIG. 1 is a flowchart illustrating a method, in accordance with an aspect of the present disclosure.

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices and methods relating to modifying biological molecules are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

As used herein, the terms "activated" and "activation" refer to T cells that are CD3+, CD4+, and/or CD8+.

As used herein the term "convolutional neural network" refers to a type of deep neural network typically consisting of a series of convolutional layers that classifies images. Convolutional neural networks operate on spatially-local regions of input images to recognize patterns in those regions. Convolutional neural networks can include fully-connected layers and other types of layers in addition to the convolutional layers.

As used herein, the term "FAD" refers to flavin adenine dinucleotide.

As used herein, the term "memory" includes a non-volatile medium, e.g., a magnetic media or hard disk, optical storage, or flash memory; a volatile medium, such as system memory, e.g., random access memory (RAM) such as DRAM, SRAM, EDO RAM, RAMBUS RAM, DR DRAM, etc.; or an installation medium, such as software media, e.g., a CD-ROM, or floppy disks, on which programs may be stored and/or data communications may be buffered. The term "memory" may also include other types of memory or combinations thereof.

As used herein, the term "NAD(P)H" refers to reduced nicotinamide adenine dinucleotide and/or reduced nicotinamide dinucleotide phosphate.

As used herein, the term "processor" may include one or more processors and memories and/or one or more programmable hardware elements. As used herein, the term "processor" is intended to include any of types of processors, CPUs, GPUs, microcontrollers, digital signal processors, or other devices capable of executing software instructions.

As used herein, the term "training" refers to a process that provides labeled data to a classification algorithm to learn to map input data to a category.

As used herein, the term "pre-training" refers to training a classifier on an initial dataset that is a different and typically larger dataset than the target dataset. As used herein, pre-training initializes a classifier so that it can by trained faster or more accurately on the target dataset.

As used herein, the term "fine-tuning" refers to use of the pre-trained model weights to initialize parameters of a new model and then train a new model on the target dataset.

The various aspects may be described herein in terms of various functional components and processing steps. It should be appreciated that such components and steps may be realized by any number of hardware components configured to perform the specified functions.

Methods

This disclosure provides a variety of methods. It should be appreciated that various methods are suitable for use with other methods. Similarly, it should be appreciated that various methods are suitable for use with the systems described elsewhere herein. When a feature of the present disclosure is described with respect to a given method, that feature is also expressly contemplated as being useful for the other methods and systems described herein, unless the context clearly dictates otherwise.

Referring to FIG. 1, the present disclosure provides a method 100 of sorting T cells. At process block 102, the method 100 includes receiving a population of T cells having unknown activation status. The population of T cells can itself be contained within a broader population of cells that includes some cells that are not T cells, such as red blood cells and the like. At process block 104, the method 100 includes acquiring an autofluorescence intensity image for each T cell of the population of T cells, thereby resulting in a set of autofluorescence intensity images. At optional process block 105, the method 100 optionally includes pre-processing the autofluorescence intensity images of the set of autofluorescence intensity images to provide a set of adjusted autofluorescence intensity images. At optional process block 106, the method 100 optionally includes physically isolating a first portion of the population of T cells from a second portion of the population of T cells based on an activation prediction. At optional process block 108, the method 100 optionally includes generating a report including an activation prediction.

The autofluorescence intensity image acquired at process block 104 can be acquired in a variety of ways, as would be understood by one having ordinary skill in the spectroscopic arts with knowledge of this disclosure and their own knowledge from the field. The specific way in which the autofluorescence intensity image is acquired is not intended to be limiting to the scope of the present invention, so long as the autofluorescence intensity images necessary for the methods described herein can be suitably measured, estimated, or determined in any fashion. One example of a suitable autofluorescence intensity image acquisition is described below in the examples section.

The optional pre-processing of process block 105 can include various image processing steps for providing better consistency of images for introduction to the convolutional neural network. The pre-processing can include cropping the autofluorescence intensity image, padding the autofluorescence intensity image (i.e., adding black pixels to a side of the image to artificially increase the image's size), rotating the autofluorescence intensity image, reflecting the autofluorescence intensity image (i.e., taking a mirror image of the original about a given axis), or a combination thereof.

The optional physically isolating of process block 106 is in response to an activation prediction determined from the acquired autofluorescence intensity image. If the activation prediction exceeds a predetermined threshold for a given T cell, then that T cell is placed into the first portion. If the activation prediction is less than or equal to the predetermined threshold for the given T cell, then that T cell is placed into the second portion. The result of this physical isolation is that the first portion of the population of T cells is significantly enriched in activated T cells, whereas the second portion of the population of T cells is significantly depleted of activated T cells.

In some cases, the physically isolating of process block 106 can include isolating cells into three, four, five, six, or more portions. In these cases, the different portions will be separated by a number of predetermined thresholds that is one less than the number of portions (i.e., three portions=two predetermined thresholds). The portion whose activation prediction exceeds all of the predetermined thresholds (i.e., exceeds the highest threshold) contains the greatest concentration of activated T cells. The portion whose activation prediction fails to exceed any of the predetermined thresholds (i.e., fails to exceed the lowest threshold) contains the lowest concentration of activated T cells. Using multiple predetermined thresholds can afford the preparation of portions of the population of T cells that have extremely high or extremely low concentrations of activated T cells.

The optional generating a report of process block 108 can include any form of report generation known to be useful in the medical arts, including but not limited to, generating a digital report, a display showing results, printing a physical hard copy of a report The report optionally identifies a proportion of the population of T cells having the activation prediction that exceeds the predetermined threshold.

The activation status is computed using a convolutional neural network. The convolutional neural network can be pre-trained with images that are not fluorescence intensity images of cells, and then it can be fine-tuned with images that are fluorescence intensity images of T cells with a known activation state.

The pre-training can include training with standard images of objects that are visible to the human eye (i.e., a neural network pre-trained to identify dogs as dogs, cats as cats, humans as humans, etc.). Various commercially-available neural networks come pre-trained in this fashion. For example, the Inception v3 convolutional neural network with pre-trained ImageNet weights discussed below utilizes this type of pre-training.

The training of the convolutional neural network involves inputting a number of autofluorescence intensity images for T cells with a known activation state. In some cases, the only input for the training of the convolutional neural network is the series of autofluorescence intensity images for T cells with a known activation state. After this training has occurred, the result is a trained convolutional neural network, which is ready to receive autofluorescence intensity images of T cells that have an unknown activation state and to make an activation prediction. The convolutional neural network can be trained with at least 100 images, at least 200 images, at least 500 images, at least 1000 images, at least 2500 images, at least 5000 images, or more images of T cells having known activation states. The trained convolutional neural network can include at least 5 layers, at least 6 layers, at least 7 layers, at least 8 layers, at least 9 layers, or at least 10 layers. The trained convolutional neural network can include at most 100 layers, at most 50 layers, at most 20 layers, at most 17 layers, at most 15 layers, at most 14 layers, at most 13 layers, or at most 12 layers. The convolutional neural network can include segmenting of the autofluorescence intensity images.

In some cases, the trained convolutional neural network can be instrument-specific. It should be appreciated that this instrument-specificity can encompass specificity for a given specific instrument or specificity for a given model of a specific instrument.

In some cases, the trained convolutional neural network can be patient-specific. In these cases, the convolutional neural network is at least partially trained with T cells having a known activation state that come from similar patients. Patient similarity can be assessed based on patient age, sex, disease subtype, or other characteristics.

In some cases, the pre-training and the training can both be done without utilizing a cell size attribute (e.g., diameter), cell morphology, or either as inputs.

The method 100 can sort CD4+, CD3+, and/or CD8+ T cells based on activation status.

The method 100 can provide surprising accuracy of classifying T cells as activated. The accuracy can be at least 85%, at least 87.5%, at least 90%, at least 92.5%, at least 95%, at least 96%, at least 97%, or at least 98%. One non-limiting example of measuring the accuracy includes executing the method 100 on a given cell with unknown activation state and then using one of the traditional methods for determining activation state (which will typically be a destructive method) for a number of cells that is statistically significant.

The method 100 can be performed without the use of a fluorescent label for binding the T cell. The method 100 can be performed without immobilizing the T cell.

In some cases, the method 100 can include a step for identifying outlier images. In particular, if the image contains no cells at all or contains cells that are not T cells (e.g., a red blood cell), then those images can be discarded and any cells corresponding to those images can also be discarded.

Figure 2:
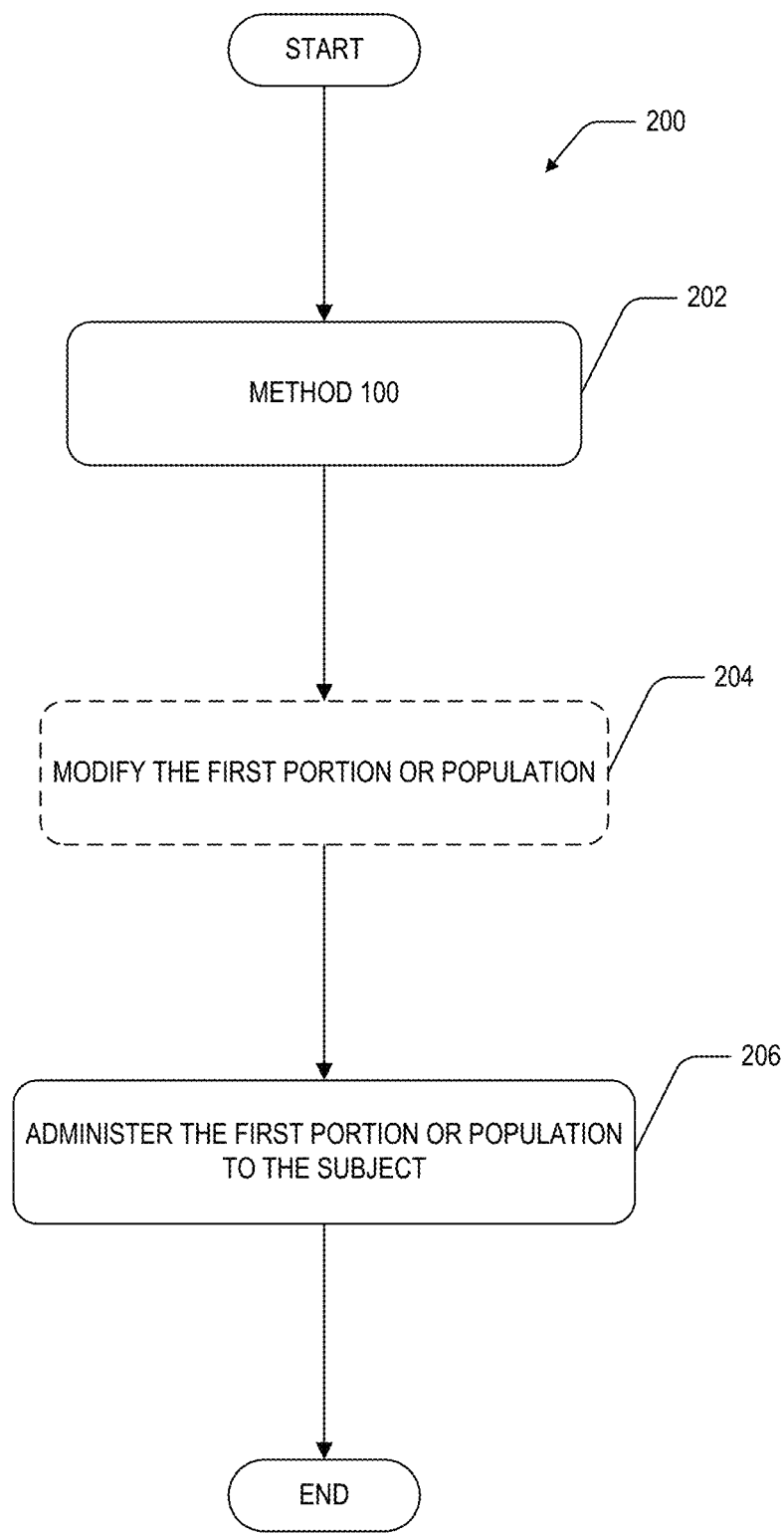
FIG. 2 is a flowchart illustrating a method, in accordance with an aspect of the present disclosure.

Referring to FIG. 2, the present disclosure provides a method 200 of administering activated T cells to a subject in need thereof. At process block 202, the method 200 includes the method 100 described above, which results in a first portion of the population of T cells enriched for activation or a population of T cells for which a report has been generated regarding activation status. At optional process block 204, the method 200 optionally includes modifying the first portion of the population of T cells (in the case where sorting did occur) or the population of T cells (in the case where the sorting did not occur). At process block 206, the method 200 includes administering the first portion of the population of T cells or the population of T cells to the subject.

The T cells can be harvested from the subject to which they are administered prior to sorting. The sorted T cells or the population of T cells can be either directly introduced to the subject or can undergo additional processing prior to introduction to the subject. In one case, the sorted T cells or the population of T cells can be modified to contain chimeric antigen receptors (CARs).

In some cases, the method of administering activated T cells can include administering an unsorted population of T cells for which the proportion of activated T cells is known to be above a given threshold (i.e., if greater than a given percentage of a population of T cells has an activation prediction that exceeds the predetermined threshold, then the entire population can be administered to the subject).

The methods described herein provided surprising results to the inventors in at least three ways. First, it was not clear at the outset whether the methods would be effective at distinguishing activated versus quiescent T cells, because it was not clear that autofluorescence intensity images could classify accurately. The efficacy itself was surprising, and the quality of the classification achieved by the methods was even more surprising. Second, the inventors expected that training models using features quantified from the images, such as cell size and/or cell morphologies, in the input to classification algorithms would improve classification, because these features are related to activation and common features for cell state classification in the microscopy domain. It was surprisingly discovered that using this information leads to worse classification than using autofluorescence intensity images. Third, the degree of classification accuracy achieved was surprising. The classification accuracy of upward of 85-95% or better that is achieved using a convolutional neural network trained only with autofluorescence images (this does not exclude pre-training using other images) and with autofluorescence images as the lone input is surprising.

Systems

This disclosure also provides systems. The systems can be suitable for use with the methods described herein. When a feature of the present disclosure is described with respect to a given system, that feature is also expressly contemplated as being combinable with the other systems and methods described herein, unless the context clearly dictates otherwise.

Figure 3:
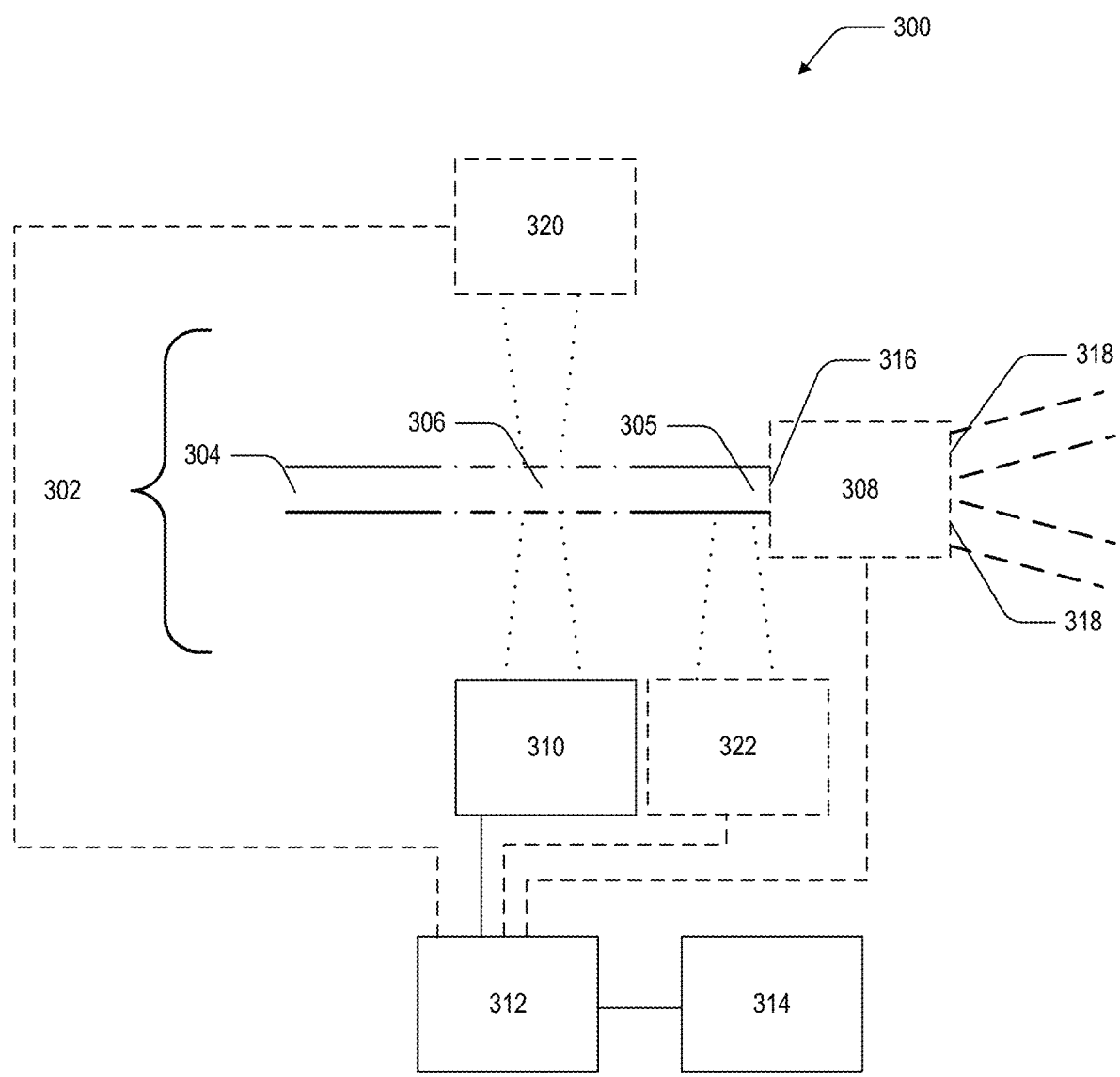
FIG. 3 is a block diagram of a device, in accordance with an aspect of the present disclosure.

Referring to FIG. 3, the present disclosure provides a T cell sorting device 300. The device 300 includes a cell analysis pathway 302. The cell analysis pathway 302 includes an inlet 304, an observation zone 306, and an outlet 305. The device 300 optionally includes a cell sorter 308. The observation zone 306 is coupled to the inlet 304 downstream of the inlet 304 and is coupled to the outlet 305 upstream of the outlet 305. The device 300 also includes a single-cell autofluorescence image sensor 310. The device 300 includes a processor 312 and a non-transitory computer-readable medium 314, such as a memory.

The inlet 304 can be any nanofluidic, microfluidic, or other cell sorting inlet. A person having ordinary skill in the art of fluidics has knowledge of suitable inlets 304 and the present disclosure is not intended to be bound by one specific implementation of an inlet 304.

The outlet 305 can be nanofluidic, microfluidic, or other cell sorting outlet. A person having ordinary skill in the art of fluidics has knowledge of suitable outlets 305 and the present disclosure is not intended to be bound by one specific implementation of an outlet 305.

The observation zone 306 is configured to present T cells for individual autofluorescence interrogation. A person having ordinary skill in the art has knowledge of suitable observation zones 306 and the present disclosure is not intended to be bound by one specific implementation of an observation zone 306.

The optional cell sorter 308 has a sorter inlet 316 and at least two sorter outlets 318. The cell sorter is coupled to the observation zone 306 via the sorter inlet 316 downstream of the observation zone 306. The cell sorter 308 is configured to selectively direct a cell from the sorter inlet 316 to one of the at least two sorter outlets 318 based on a sorter signal.

The inlet 304, observation zone 306, outlet 305, and optional cell sorter 308 can be components known to those having ordinary skill in the art to be useful in flow sorters, including commercial flow sorters. The cell analysis pathway can further optionally include a flow regulator, as would be understood by those having ordinary skill in the art. The flow regulator can be configured to provide flow of cells through the observation zone at a rate that allows the single-cell autofluorescence image sensor 310 to acquire the autofluorescence intensity image. A useful review of the sorts of fluidics that can be used in combination with the present disclosure is Shields et al., "Microfluidic cell sorting: a review of the advances in the separation of cells from debulking to rare cell isolation," *Lab Chip*, 2015 Mar. 7; 15(5): 1230-49, which is incorporated herein by reference in its entirety.

The single-cell autofluorescence image sensor 310 can be any detector suitable for acquiring single-cell autofluorescence images as understood by those having ordinary skill in the optical arts. It should be appreciated that these images need not be acquired by acquiring all pixels simultaneously, so autofluorescence images acquired by point- and/or line-scanning methods are expressly contemplated. Examples of suitable single-cell autofluorescence image sensors 310 include, but are not limited to, a camera, a photodiode array, a streak camera, a charge capture device array, a photodiode, an avalanche photodiode, a photomultiplier tube, combinations thereof, and the like.

The single-cell autofluorescence image sensor 310 can be directly (i.e., the processor 312 communicates directly with the detector 310 and receives the signals) or indirectly (i.e., the processor 312 communicates with a sub-controller that is specific to the sensor 310 and the signals from the sensor 310 can be modified or unmodified before sending to the processor 312) controlled by the processor 312. Fluorescence intensity images can be acquired by known imaging methods. The device 300 can include various optical filters tuned to isolate autofluorescence signals of interest. The optical filters can be tuned to the autofluorescence wavelengths of NAD(P)H and/or FAD.

The device 300 can optionally include a light source 320 for optically exciting the cells to initiate autofluorescence. Suitable light sources 320 include, but are not limited to, lasers, LEDs, lamps, filtered light, fiber lasers, and the like. The light source 320 can be continuous wave. The light source 320 can be pulsed, which includes sources that are naturally pulsed and continuous sources that are chopped or otherwise optically modulated with an external component. The light source 320 can provide pulses of light having a full-width at half maximum (FWHM) pulse width of between 1 fs and 10 ns. In some cases, the FWHM pulse width is between 30 fs and 1 ns. The light source 320 can emit wavelengths that are tuned to the absorption of NAD(P)H and/or FAD.

The single-cell autofluorescence image sensor 310 can be configured to acquire the autofluorescence dataset at a repetition rate of between 1 kHz and 20 GHz. In some cases, the repetition rate can be between 1 MHz and 1 GHz. In other cases, the repetition rate can be between 20 MHz and 100 MHz. The light source 320 can be configured to operate at these repetition rates.

The device 300 can optionally include a cell size measurement tool 322. The cell size measurement tool 322 can be any device capable of measuring the size of cells, including but not limited to, an optical microscope. In some cases, the single-cell autofluorescence image sensor 310 and the cell size measurement tool 322 can be integrated into a single optical subsystem. While some aspects of the methods described herein can operate by not utilizing the cell size as an input to the convolutional neural network, it may be useful to measure the cell size for other purposes.

The processor 312 is in electronic communication with the detector 310 and the cell sorter 308. The processor 312 is also in electronic communication with, when present, the optional light source 320 and the optional cell size measurement tool 322.

The non-transitory computer-readable medium 314 has stored thereon instructions that, when executed by the processor, cause the processor to execute at least a portion of the methods described herein. The trained convolutional neural network can be stored in the non-transitory computer-readable medium 314. The non-transitory computer-readable medium 314 can be local to the device 300 or can be remote from the device, so long as it is accessible by the processor 312.

The device 300 can be substantially free of fluorescent labels (i.e., the cell analysis pathway 302 does not include a region for mixing the cell(s) with a fluorescent label). The device 300 can be substantially free of immobilizing agents for binding and immobilizing T cells.

Example 1

Cell Preparation and Imaging

This study was approved by the Institutional Review Board of the University of Wisconsin-Madison (#2018-0103). Informed consent was obtained from all donors. The NAD(P)H intensity images in this study were created from a subset of the NAD(P)H fluorescence lifetime images acquired in Walsh, A. et al. Label-free Method for Classification of T cell Activation. bioRxiv (2019); DOI 10.1101/536813; ("Walsh et al."), which is incorporated herein in its entirety by reference. CD3 and CD8 T cells were isolated using negative selection methods (RosetteSep, StemCell Technologies) from the peripheral blood of 6 healthy donors (3 male, 3 female, mean age=26). The T cells were divided into quiescent and activated groups, where the activated group was stimulated with a tetrameric antibody against CD2, CD3, and CD28 (StemCell Technologies). T cell populations were cultured for 48 hours at 37 C, 5% CO2, and 99% humidity.

NAD(P)H intensity images were created by integrating the photon counts of fluorescence lifetime decays at each pixel within the fluorescence lifetime images acquired, as described by Walsh et al. Briefly, images were acquired using an Ultima (Bruker Fluorescence Microscopy) two-photon microscope coupled to an inverted microscope body (TiE, Nikon) with an Insight DS+ (Spectra Physics) as the excitation source. A 100× objective (Nikon Plan Apo Lambda, NA 1.45), lending an approximate field of view of 110 μm, was used in all experiments with the laser tuned to 750 nm for NAD(P)H two-photon excitation and a 440/80 nm bandpass emission filter in front of a GaAsP photomultiplier tube (PMT; H7422, Hamamatsu). Images were acquired for 60 seconds with a laser power at the sample of 3.0-3.2 mW and a pixel dwell time of 4.6 μs. Grayscale microscopy images were labeled with a deidentified donor ID and T cell activity state according to the culture conditions: quiescent for T cells not exposed to the activating antibodies or activated for T cells exposed to the activating antibodies.

Image Processing

We segmented cell images using CellProfiler, which is described in Carpenter, A. E. et al. CellProfiler: image analysis software for identifying and quantifying cell phenotypes. Genome Biol. 7, R100 (2006); DOI 10.1186/gb-2006-7-10-r100; which is incorporated herein in its entirety by reference. Each cell was cropped according to the bounding box of its segmented mask. Cell short NAD(P)H lifetime was used to filter out other visually indistinguishable cells (e.g., red blood cells) by removing cells with a mean fluorescence lifetime less than 200 ps. To remove very dim images and images containing no cells, we further filtered the segmented images by thresholding the combination of image entropy and total intensity. The segmented images were removed from the dataset if their entropy was less than 4 or if their entropy was less than 4.7 and their intensity was less than 3500. The threshold values were chosen based on the distribution of entropy and intensity with a Gaussian approximation. This filter was conservative. We manually inspected the removed images to ensure none of them contained T cells.

Because the classifiers that used image pixels as input required uniform size and some required square images, we padded all activated and quiescent cell images with black borders. The padding size of 82×82 was chosen based on the largest image in the dataset after removing extremely large outliers. Also, we augmented the dataset by rotating each original image by 90; 180; and 270 degrees and flipping it horizontally and vertically. We implemented this image processing pipeline using the Python package OpenCV.

Bradski, G. The OpenCV Library. *Dr. Dobb's J. Softw. Tools* (2000), which is incorporated herein in its entirety by reference.

Nested Cross-Validation

We trained and evaluated eight classifiers of increasing complexity (Table 1). We used the same leave-one-donor-out test principle to measure the performance of all models. For example, when using donor 1 as the test donor, the frequency classifier counts the positive proportion among all images in the augmented dataset from donor 2, 3, 5, and 6. Then, it uses this frequency to predict the activity for all unaugmented images from donor 1. By testing in this way, the classification result tells us how well each model performs on images from new donors. Donor 4 was not included in this cross-validation because we randomly selected it as a complete hold-out donor. All images from donor 4 were only used after hyper-parameter tuning and model selection as a final independent test to assess the generalizability of our pipeline to a new donor.

TABLE 1

| Model | Description |
| --- | --- |
| Frequency Classifier | Predict class probability using the class frequencies in the training set. |
| Logistic Regression with Pixel Intensity | Regularized logistic regression model fitted with the image pixel intensity matrix (82 × 82). Regularization power $\lambda$ of $l_1$ penalty is tuned. |
| Logistic Regression with Total Intensity and Size | Regularized logistic regression model fitted with two numerical values: image total intensity and cell mask size. Regularization power $\lambda$ of $l_1$ penalty is tuned. |
| Logistic Regression with CellProfiler Features | Regularized logistic regression model fitted with 123 features extracted from CellProfiler related to intensity, texture, and area. Regularization power $\lambda$ of $l_1$ penalty is tuned. |
| One-layer Fully Connected Neural Network | Fully connected one-hidden-layer neural network with pixel intensity as input. Number of neurons, learning rate, and batch size are tuned. |
| LeNet CNN | CNN with the LeNet architecture with pixel intensity as input. Learning rate and batch size are tuned. |
| Pre-trained CNN Off-the-shelf Model | Freeze layers of a pre-trained Inception v3 CNN. Train a final added layer from scratch with extracted off-the-shelf features. Learning rate and batch size are tuned. |
| Pre-trained CNN with Fine-tuning | Fine-tune the last n layers of a pre-trained Inception v3 CNN. The layer number n, learning rate, and batch size are tuned. |

Figure 11:
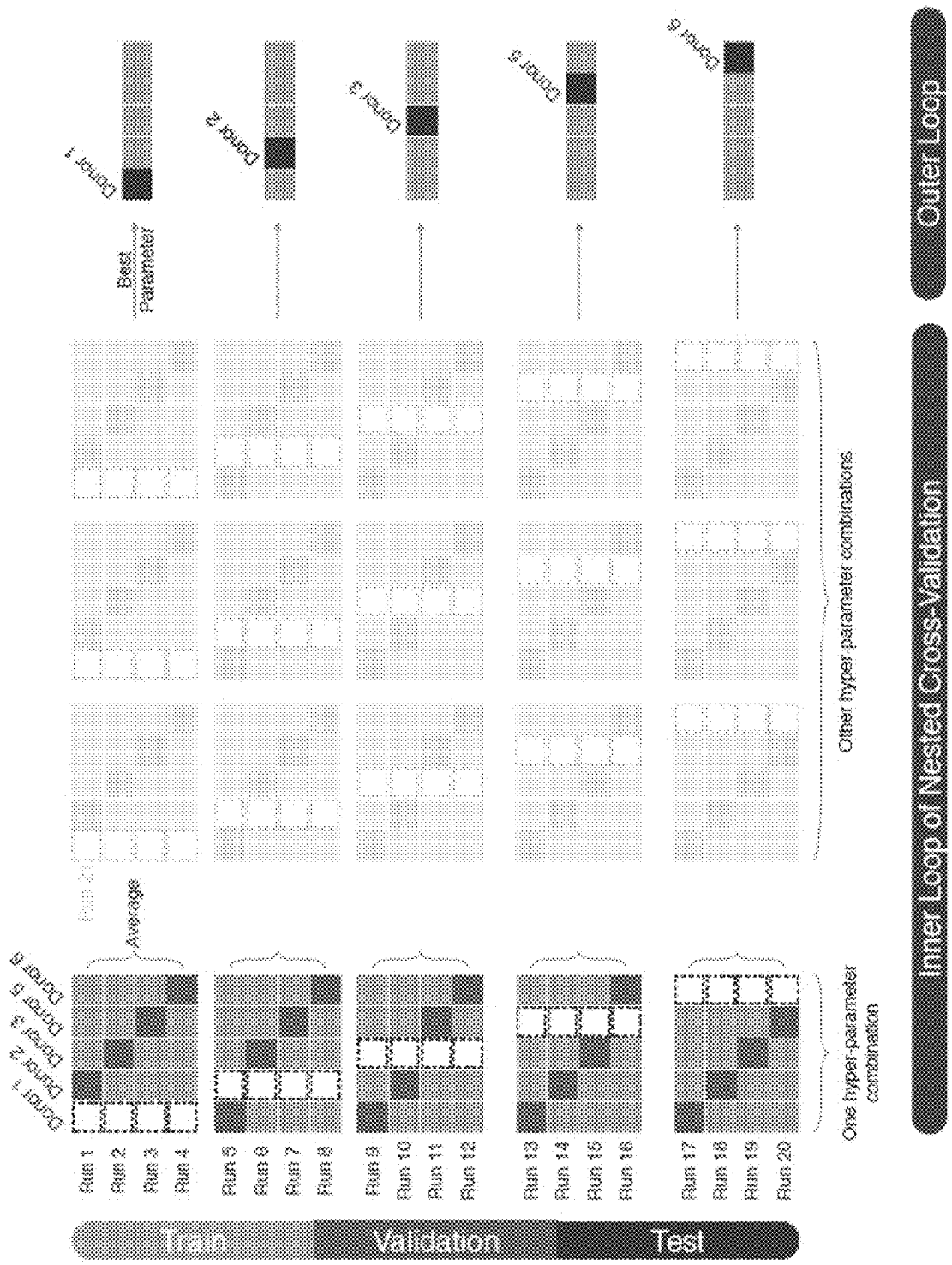
FIG. 11 shows a 5×4 nested cross-validation scheme, as discussed in Example 1. For each test donor (blue), we used an inner cross-validation loop to optimize the hyper-parameters. We trained a model for each hyper-parameter combination using the training donors' augmented images (yellow) and selected the hyper-parameters that performed best on the validation donor's images (green). The validation donor is sometimes referred to as a tuning donor in cross-validation. Then, we trained a final model for each test donor using the selected hyper-parameters.

Following the leave-one-donor-out test principle, we wanted the selection of the optimal hyper-parameters to be generalizable to new donors as well. Therefore, we applied a nested cross-validation scheme (FIG. 11). For each test donor, within the inner loop we performed 4-fold cross-validation to measure the average performance of each hyper-parameter combination (grid search). Each fold in the inner loop cross-validation corresponds to one donor's augmented images. The outer cross-validation loop used the selected hyper-parameters from the inner loop cross-validation to train a new model with the four other donors' augmented images. We evaluated the trained model on the outer loop test donor. For models requiring early stopping, we constructed an early stopping set by randomly sampling one-fourth of the unaugmented images from the training set and removing their augmented copies. Then, training continued as long as the performance on images in the early stopping set improved. Similarly, we did not include augmented images in the validation set or the test set.

No single evaluation metric can capture all the strengths and weaknesses of a classifier, especially because our dataset was class imbalanced and not skewed in the same way for all donors. Therefore, we considered multiple evaluation metrics in the outer loop. Accuracy measures the percentage of correct predictions. It is easy to interpret, but it does not necessarily characterize a useful classifier. For example, when positive samples are rare, a trivial classifier that predicts all samples as negative yields high accuracy. Precision and recall (sensitivity), on the other hand, consider the costs of false positive and false negative predictions, respectively. Graphical metrics like the receiver operator characteristic (ROC) curve and precision recall (PR) curve avoid setting a specific classification threshold. We used area under the curve (AUC) to summarize ROC curves and average precision for the PR curves. The ROC curve is independent of the class distribution, while the PR curve is useful when the classes are imbalanced. See, Lever, J., Krzywinski, M. & Altman, N. Points of Significance: Classification evaluation. Nat. Methods 13, 603-604 (2016); DOI 10.1038/nmeth.3945; which is incorporated herein in its entirety by reference. For this reason, we used mean average precision of the inner loop 4-fold cross-validation to select optimal hyper-parameters.

During the nested cross-validation, we trained the LeNet CNN and pre-trained CNN with fine-tuning using GPUs. These jobs ran on GTX 1080, GTX 1080 Ti, K40, K80, P100, or RTX 2080 Ti GPUs. All other models were trained using CPUs.

Linear Classifiers

We used a trivial frequency classifier as a baseline model. This model computes the positive sample percentage in the training set. Then, it uses this frequency as a positive class prediction score (between 0 and 1) for all samples in the test set.

Logistic regression with Lasso regularization is a standard and interpretable statistical model used to classify microscopy images. See, Pavillon, N., Hobro, A. J., Akira, S. & Smith, N. I. Noninvasive detection of macrophage activation with single-cell resolution through machine learning. Proc. Natl. Acad. Sci. 115, E2676-E2685 (2018); DOI 10.1073/pnas.1711872115, which is incorporated herein in its entirety by reference. The Lasso approach reduces the number of effective parameters by shrinking the parameters of less predictive features to zero. These features are ignored when making a new prediction. We fitted and tested three Lasso logistic regression models with different types of features using the Python package scikit-learn. See, Pedregosa, F. et al. Scikit-learn: Machine Learning in Python. J. Mach. Learn. Res. 12, 2825-2830 (2011), which is incorporated herein in its entirety by reference. An image intensity matrix with dimension 82×82 and values from 0 to 255, reshaped into a vector with length 6,724, was used to fit the first model. The second model was trained with two scalar features, cell size and image total intensity, where cell size was computed using the pixel count in the cell mask generated by CellProfiler. The last model used 123 features relating to cell intensity, texture, and area, which were extracted from cell images using a CellProfiler pipeline with modules MeaureObjectSizeShape, MeasureObjectIntensity, and Measure Texture. The Lasso regularization parameter $\lambda$ was tuned for all three classifiers with nested cross-validation (Table 2). We also applied inverse class frequencies in the training data as class weights to adjust the imbalanced dataset.

TABLE 2

| Model | Hyper-parameter | Candidate |
|---|---|---|
| Logistic Regression Models | λ | 0.001, 0.01, 0.1, 1, 10, 100, 1000, 10000 |
| One-layer Fully Connected Neural Network | Learning Rate | 0.1, 0.01, 0.001, 0.0001, 0.00001 |
| | Batch Size | 8, 16, 32, 64 |
| | Neuron Number | 16, 64, 128, 512, 1024 |
| LeNet Cnn | Learning Rate | 0.1, 0.01, 0.001, 0.0001, 0.00001 |
| | Batch Size | 8, 16, 32, 64 |
| Pre-trained CNN Off-the-shelf Model | Learning Rate | 0.01, 0.001, 0.0001, 0.00001 |
| | Batch Size | 8, 16, 32, 64 |
| Pre-trained CNN with Fine-tuning | Learning Rate | 0.01, 0.001, 0.0001, 0.00001 |
| | Batch Size | 8, 16, 32, 64 |
| | n | 1, 2, 3, 4, 5, 6, 7, 8, 9, 10, 11 |

Simple Neural Network Classifiers

We developed a simple fully-connected neural network with one hidden layer using the Python package Keras with the TensorFlow backend. See, Chollet, F. & others. Keras (2015); and Martin Abadi et al. TensorFlow: Large-Scale Machine Learning on Heterogeneous Systems (2015), both of which are incorporated herein in their entirety by reference. The input layer uses the image pixel matrix with dimension 82×82. Network hyper-parameters—hidden neuron numbers, learning rate, and batch size—were tuned using nested cross-validation (Table 2). The cross-entropy loss function was weighted according to the class distribution in the training set.

Also, we trained a CNN with the LeNet architecture (see, Lecun, Y., Bottou, L., Bengio, Y. & Haffner, P. Gradient-based learning applied to document recognition. Proc. IEEE 86, 2278-2324 (1998); DOI 10.1109/5.726791, which is incorporated herein in its entirety by reference) with randomly initialized weights (no pre-training). The LeNet architecture has two convolutional layers and two pooling layers. We used the default number of neurons specified in the original paper in each layer. The input layer was modified to support 82×82 one-channel images, so we could train this network with image pixel intensities. Similar to the fully-connected neural network, we used nested cross-validation to tune the learning rate and batch size (Table 2) and applied class weighting. We used early stopping with a patience of 10 for both models, which means we stopped training if the loss function failed to improve on the early stopping set in 10 consecutive epochs.

Pre-Trained CNN Classifiers

Figure 12:
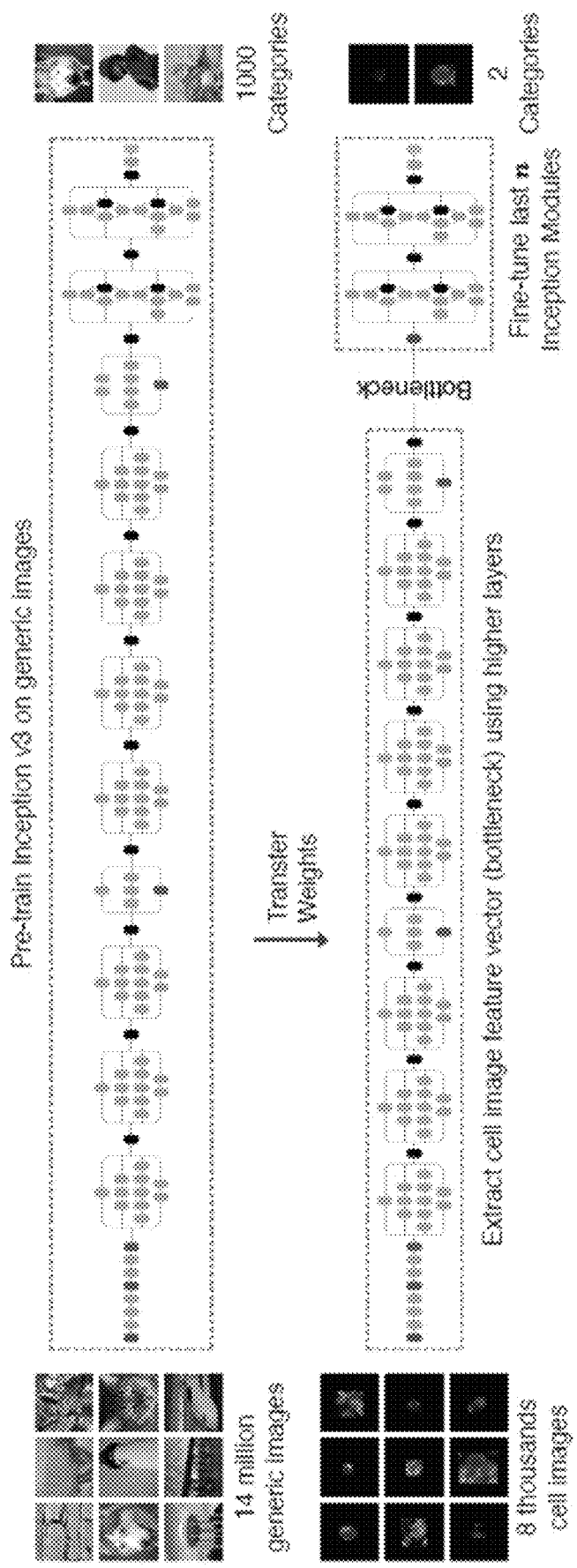
FIG. 12 is a visual representation of fine-tuning of the Inception v3 CNN to predict T cell activity, as described in Example 1. The generic image examples are adapted from ImageNet.

We developed a transfer learning classifier that uses the Inception v3 CNN with pre-trained ImageNet weights. See, Szegedy, C., Vanhoucke, V., Ioffe, S., Shlens, J. & Wojna, Z. Rethinking the Inception Architecture for Computer Vision; arXiv:1512.00567 [cs] (2015); and Deng, J. et al. ImageNet: A Large-Scale Hierarchical Image Database. In CVPR09 (2009), both of which are incorporated herein in their entirety by reference. Instead of training the whole network end-to-end from scratch, we took advantage of the pre-trained weights by extracting and modeling off-the-shelf features or fine-tuning the last n Inception modules, where n was treated as a hyper-parameter (FIG. 12). Inception modules are mini-networks that constitute the overall Inception v3 architecture. The first approach is a popular practice for transfer learning with Inception v3. We freeze the weights of all layers before the output layer and use them to extract generic image characteristics. Then, we train a light-weight classifier from scratch, specifically a neural network with an average pooling layer and a fully connected hidden layer with 1024 neurons, using these off-the-shelf features. We refer to this model as the pre-trained CNN off-the-shelf model. An alternative is to fix some earlier layers and fine-tune the higher-level n layers by initializing them with pre-trained weights and continuing training on a new dataset. For this model, we modified the output layer to support binary classification, and we did not add new layers. In addition, we used the nested cross-validation scheme to optimize n along with the learning rate and batch size (Table 2), creating the pre-trained CNN with fine-tuning.

To implement these two pre-trained CNN models, we resized the padded cell images with bilinear interpolation to fit the input layer dimension (299×299×3) and generated three-channel images by merging three copies of the same grayscale image. For the pre-trained CNN with fine-tuning, we first used the resized cell images to generate intermediate features ("bottlenecks"). Then, we used these features to fine-tune a sub-network. This approach significantly shortened the training time. Finally, we used class weighting and early stopping with a patience of 10 for both models. We implemented these two models using Keras with the TensorFlow backend.

Pre-Trained CNN Interpretation

We implemented multiple approaches for interpreting the pre-trained CNNs. Computing classification confidence on misclassified images can help us understand why classifiers make certain errors. The Softmax score is sometimes used as a confidence prediction. Softmax is a function that maps the output real-valued number (Logit) from a neural network into a score between 0 and 1, which is then used to make a classification as a class probability. However, using the Softmax score from a neural network as a confidence calibration does not match the real accuracy. Therefore, we used temperature scaling to better calibrate the predictions. See, Guo, C., Pleiss, G., Sun, Y. & Weinberger, K. Q. On Calibration of Modern Neural Networks; arXiv:1706.04599 [cs] (2017), which is incorporated herein in its entirety by reference. After training, for each donor, we optimized the temperature T on the nested cross-validation outer loop validation set. Then, we applied T to scale the Logit before Softmax computation and used the new Softmax score to infer classification confidence.

In addition to confidence calibration, we used dimension reduction to investigate the high-dimensional representations learned by our pre-trained CNN models. Dimension reduction is a method to project high-dimensional features into lower dimensions while preserving the characteristics of the data. Therefore, it provides a good way to visualize how trained models represent different cell image inputs. In our study, we choose UMAP (see, McInnes, L., Healy, J. & Melville, J. UMAP: Uniform Manifold Approximation and Projection for Dimension Reduction; arXiv:1802.03426 [cs, stat] (2018); and McInnes, L., Healy, J., Saul, N. & GroBberger, L. UMAP: Uniform Manifold Approximation and Projection. J. Open Source Softw. 3, 861 (2018); DOI 10.21105/joss.00861, both of which are incorporated herein in their entirety by reference) as our dimension reduction algorithm. UMAP uses manifold learning techniques to reduce feature dimensions. It arguably preserves more of the global structure and is more scalable than the standard form of t-SNE (see, Maaten, L. v. d. & Hinton, G. Visualizing data using t-SNE. J. Mach. Learn. Res. 9, 2579-2605 (2008), which is incorporated herein in its entirety by reference), an alternative approach. Using UMAP, we projected the image features, extracted from the CNN layer right before the output layer, from 2048 dimensions to two dimensions. We used the default UMAP parameter values: "n neighbors" as 15, "metrics" as "euclidean", and "min dist" as 0:1. Then, we visualized and analyzed these projected features of T cell images using 2D scatter plots. When comparing UMAP with t-SNE, we used the default t-SNE parameters: "perplexity" as 30 and "metric" as "euclidean".

For the pre-trained CNN with fine-tuning, each test donor has different tuned hyper-parameters and a different fine-tuned CNN. Therefore, we performed feature extraction and dimension reduction independently for each test donor. There is no guarantee that these five scatter plots share the same 2D basis. In contrast, the image pixel features, CellProfiler features, and off-the-shelf last layer features from a pre-trained CNN do not vary by test donor. For these three UMAP applications, we performed feature extraction and dimension reduction in one batch for all donors simultaneously. We excluded donor 4 from the dimension reduction analyses.

Finally, we used saliency maps to further analyze what morphology features were used in classification. See, Simonyan, K., Vedaldi, A. & Zisserman, A. Deep Inside Convolutional Networks: Visualising Image Classification Models and Saliency Maps; arXiv:1312.6034 [cs](2013), which is incorporated herein in its entirety by reference. A saliency map is a straightforward and efficient way to detect how prediction value changes with respect to a small change in the input cell image pixels. It is generated by computing the gradient of the output class score with respect to the input image. We compared two ways to compute this gradient: standard backpropagation and guided backpropagation. See, Springenberg, J. T., Dosovitskiy, A., Brox, T. & Riedmiller, M. Striving for Simplicity: The All Convolutional Net; arXiv:1412.6806 [cs](2014), which is incorporated herein in its entirety by reference. Backpropagation is a method to calculate the gradient of loss function with respect to the neural network's weights. Guided backpropagation is a variant that only backpropagates positive gradients. We generated saliency maps of the output layer for the pre-trained CNN with fine-tuning model for test donor 1 with a few randomly sampled images from the test set. The saliency map interpretations help us assess whether the classification basis is intuitive and whether the predictions derive from image artifacts instead of cell morphology.

Results: Overview

Our goal is to classify individual T cells as activated (positive instances) or quiescent (negative instances) using only cropped autofluorescence intensity cell images. We explore multiple classification approaches of increasing complexity. A frequency classifier uses the frequency of positive samples in the training set as the probability of the activated label. This naive baseline model assesses how well the class skew in the training images can predict the label of new images. In addition, we test three Lasso logistic regression approaches on different featurizations of the cropped T cell images. The first uses the image pixel intensities directly as features. The second uses only two image summaries as features, the cell size and total intensity. The third uses attributes calculated with CellProfiler, such as the mean intensity value and cell perimeter.

We also assess multiple types of neural networks. A fully connected neural network (multilayer perceptron) generalizes the logistic regression model with pixel intensities by adding a single hidden layer. The LeNet CNN architecture learns convolutional filters that take advantage of the image structure of the input data. This CNN is simple enough to train from random initialization with a limited number of images. Finally, we consider two deeper and more complex CNNs. Both use transfer learning to initialize the Inception v3 CNN architecture with a model that has been pre-trained on generic (nonbiological) images. One version trains a new fully connected layer from scratch using off-the-shelf features extracted from cell images with the pre-trained CNN. An alternative fine-tunes multiple layers of the pre-trained CNN.

Figure 4:
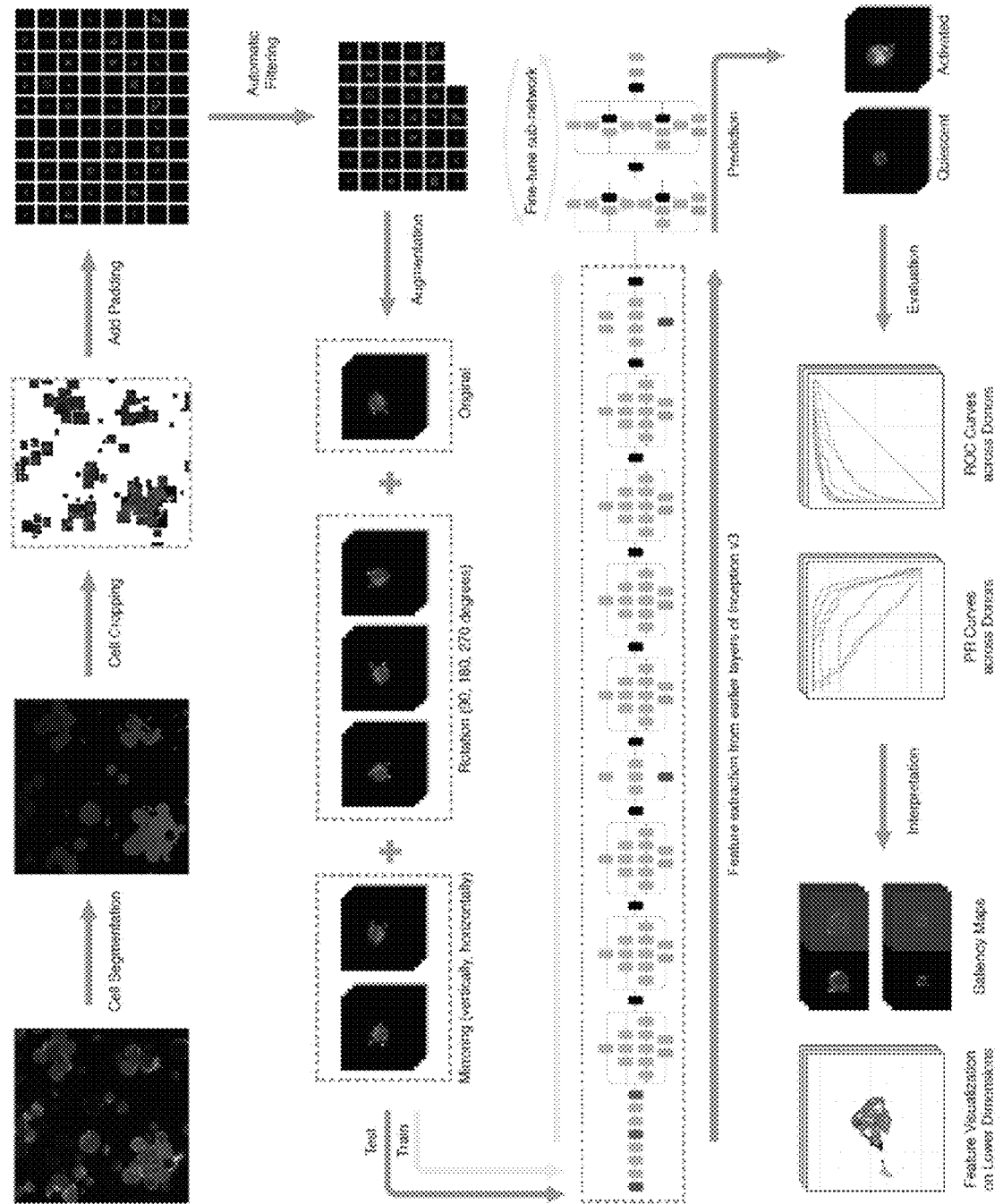
FIG. 4 is one exemplary T cell image data processing workflow, as described in the present disclosure and Example 1.

The overall workflow for our pre-trained CNN model is described in FIG. 4. The original microscopy images are segmented, cropped, and padded. We filter images that do not contain a T cell and other artifacts, leaving the final image counts for each of the six donors shown in Table 3. Then we train, evaluate, and interpret the machine learning models. FIG. 4 shows the training procedure for the pre-trained CNN as an example.

TABLE 3

|  | Donor 1 | Donor 2 | Donor 3 | Donor 4 | Donor 5 | Donor 6 |
| --- | --- | --- | --- | --- | --- | --- |
| Initial Activated | 609 | 1139 | 604 | 789 | 791 | 531 |
| Initial Quiescent | 2184 | 399 | 2351 | 2110 | 528 | 1007 |
| Final Activated | 235 | 647 | 446 | 482 | 683 | 442 |
| Final Quiescent | 1551 | 141 | 1238 | 1569 | 246 | 580 |

The T cell microscopy images may vary from donor to donor. A trained model must be able to generalize to new donors in order to be useful in a practical pre-clinical or clinical setting. Therefore, all of our evaluation strategies train on images from some donors and evaluate the trained models on separate images from a different donor, which is referred to as subject-wise cross-validation or a leave-one-patient-out scheme. We initially assess the classifiers with cross-validation across donors. In addition, we hold out all images from a randomly selected donor, donor 4, and only use them after completing the rest of our study to confirm that our model selection and hyper-parameter tuning strategies generalize to a new donor.

Results: Cross-Validation Across Donors

Figure 5:
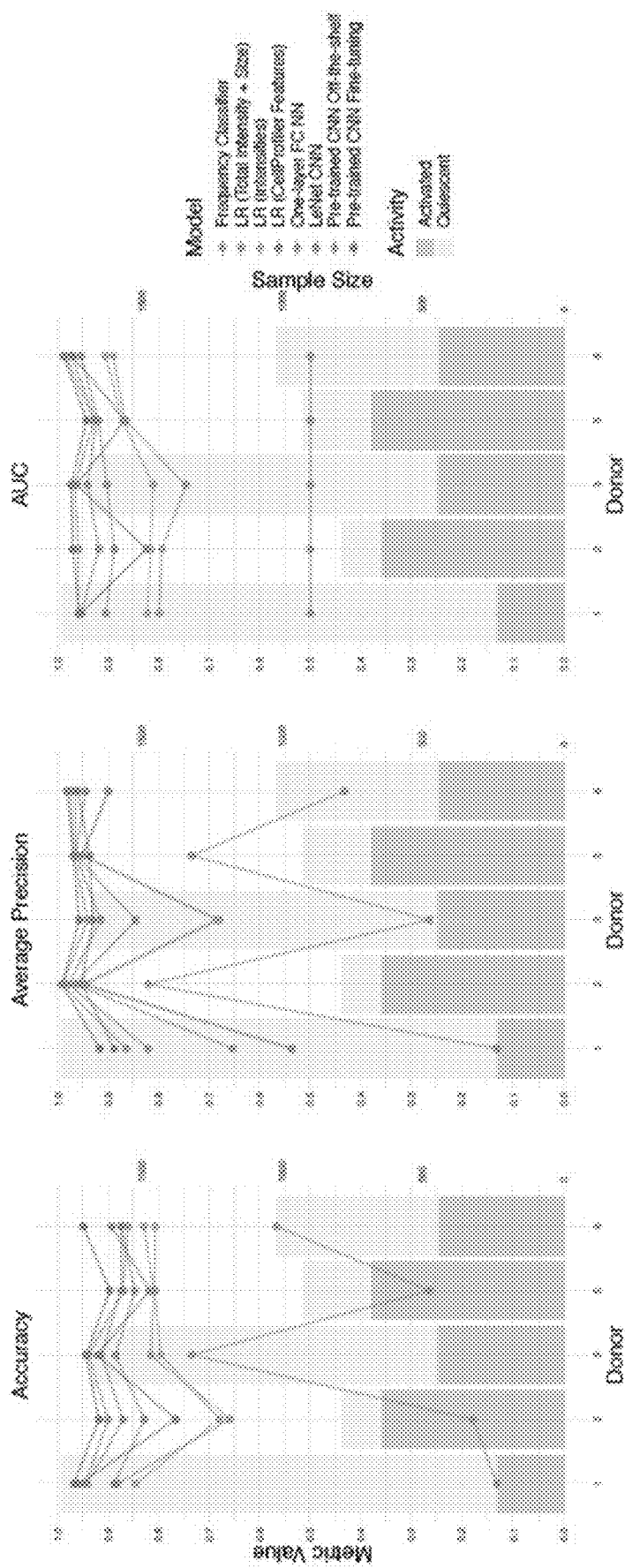
FIG. 5 is a model summary per donor for three different evaluation metrics, as described in Example 1. The line graphs display the classifiers' performance across donors. The bar graphs display the number of activated and quiescent images for each donor, which affects the classifiers' performance.
Figure 6:
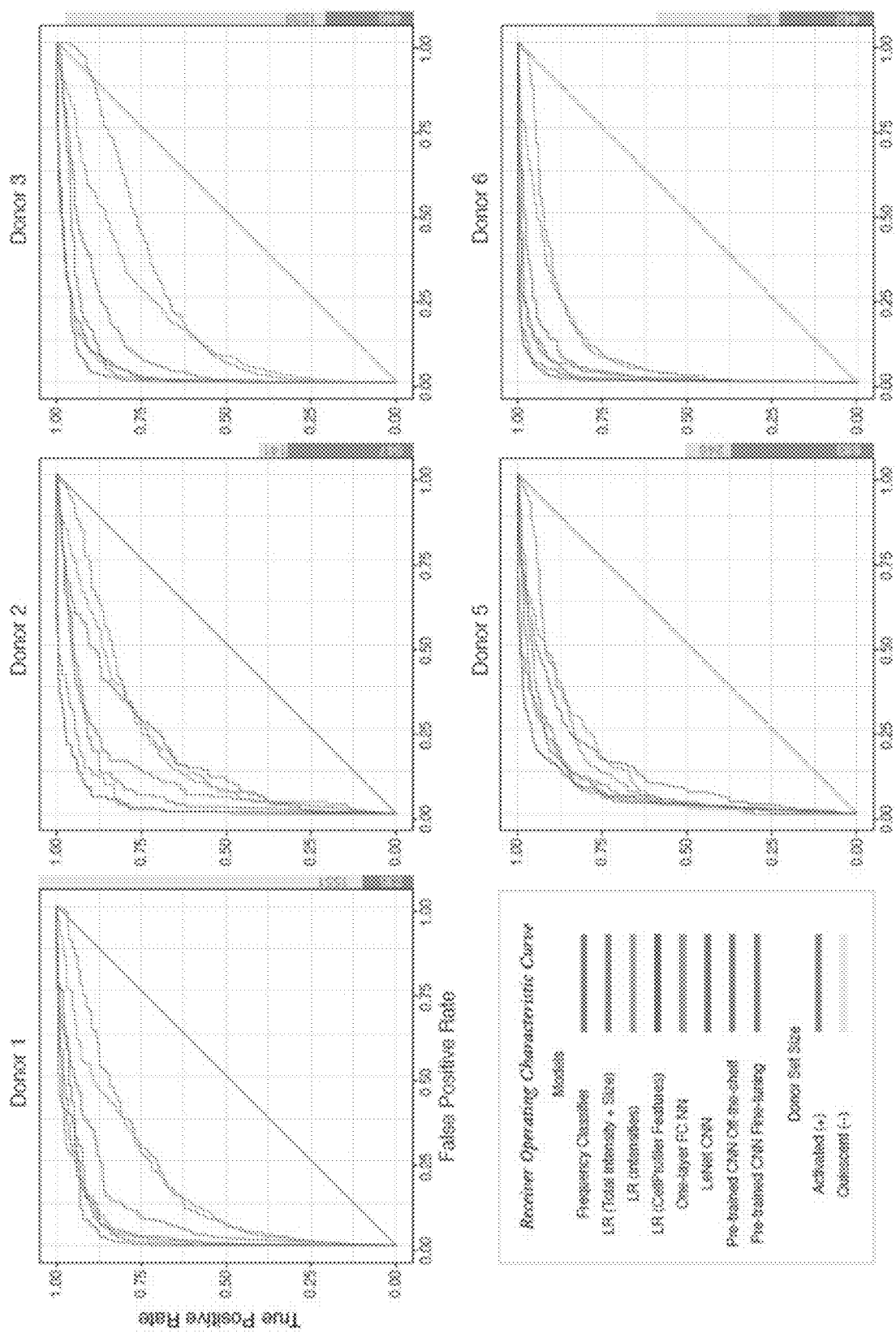
FIG. 6 shows receiver operating characteristic (ROC) curves for each type of classifier and donor, as described in Example 1. The gray bars to the right display the number of activated and quiescent images for each donor.
Figure 7:
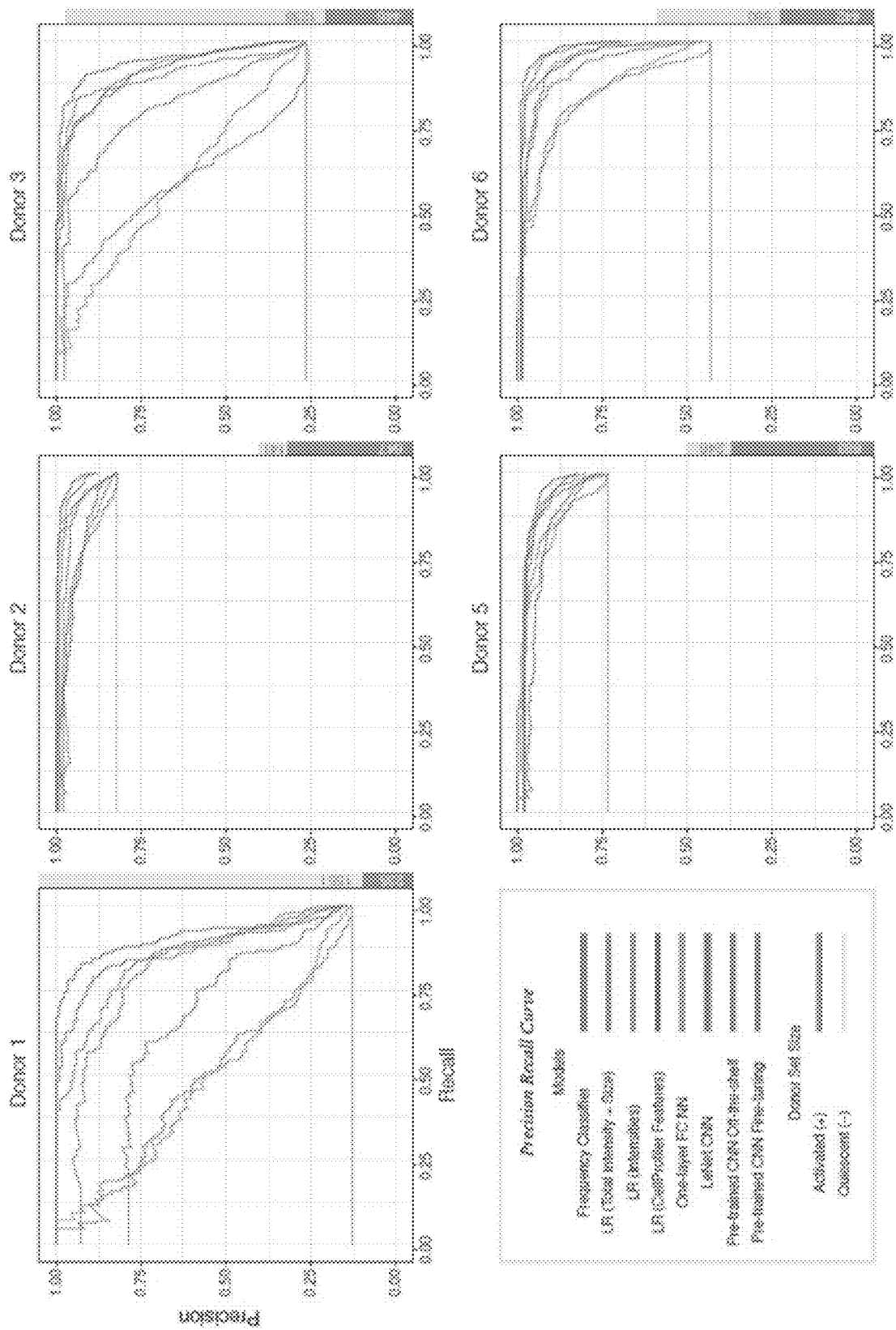
FIG. 7 shows precision recall (PR) curves for each type of classifier and donor, as described in Example 1. The gray bars to the right display the number of activated and quiescent images for each donor.

In order to assess our classifiers' performance on cell images from new donors, we design a nested cross-validation scheme to train, tune, and test all models. Due to this cross-validation design, the same model could have different optimal hyperparameters for different test donors. Therefore, we group the final model performance by test donors (FIG. 5). We plot multiple evaluation metrics because each metric rewards different behaviors. The area under the curve (AUC) and average precision are summary statistics of the receiver operating characteristic (ROC) curve (FIG. 6) and precision recall (PR) curve (FIG. 7), respectively. For all three evaluation metrics, the two pre-trained CNN models outperform other classifiers.

The frequency classifier's average accuracy for all test donors is 37.56% (FIG. 5 and Table 4). The low accuracy of this simple method implies that the majority class in the training and test sets is likely to be different. For example, there are more activated cells from donor 1 while there are more quiescent cells from the combination of donors 2, 3, 5, and 6. This baseline establishes that classifiers that fail to use features other than the label count will perform poorly.

TABLE 4

| Donor | Accuracy | Precision | Recall | Average Precision | AUC | Activated Count | Quiescent Count |
|---|---|---|---|---|---|---|---|
| 1 | 13.16% | 13.16% | 100.00% | 13.16% | 50.00% | 235 | 1551 |
| 2 | 17.89% | 0.00% | 0.00% | 82.11% | 50.00% | 647 | 141 |
| 3 | 73.52% | 0.00% | 0.00% | 26.48% | 50.00% | 446 | 1238 |
| 5 | 26.48% | 0.00% | 0.00% | 78.52% | 50.00% | 683 | 246 |
| 6 | 56.75% | 0.00% | 0.00% | 43.25% | 50.00% | 442 | 580 |

Three logistic regression models using different features all give better classifications than the baseline model. Logistic regression with the image pixel matrix leads to an average accuracy of 78.74% (FIG. 5 and Table 5). Among those 6,724 pixel features, 5,822 features on average are removed by the Lasso regularization. To interpret this model, we plot the exponential of each pixel's coefficient to visualize the odds ratios. This model learns the shape of cells (see, FIG. S1 of Appendix A of U.S. Provisional Patent Application No. 62/886,139, which is incorporated herein in its entirety by reference). Larger cells are more likely to be classified as activated. Logistic regression using only mask size and total intensity as features gives slightly better performance with an average accuracy of 79.93% (FIG. 5 and Table 6). For all test donors, the optimal coefficient of cell mask size is negative, whereas the coefficient of total intensity is positive. In practice, we expect larger cells to be activated, but the negative coefficient indicates the model learns the wrong relationship of cell size and activity state. This can be explained by the inconsistent cell size distribution across donors (see, FIG. S2 of Appendix A of U.S. Provisional Patent Application No. 62/886,139, which is incorporated herein in its entirety by reference) and the correlation of cell size and total intensity (multicollinearity). Comparing the odds ratio of one standard deviation increment of each feature, however, shows this logistic regression model is much more sensitive to total intensity than cell size. Finally, the logistic regression model with CellProfiler attributes yields 87.14% average accuracy (FIG. 5 and Table 7). After computing the odds ratio adjusting to the standard deviation of each feature, attributes that are related to image intensity and cell area have the strongest impact on the predictions.

TABLE 5

| Donor | Accuracy | Precision | Recall | Average Precision | AUC | Activated Count | Quiescent Count |
|---|---|---|---|---|---|---|---|
| 1 | 84.60% | 43.79% | 60.00% | 53.90% | 82.27% | 235 | 1551 |
| 2 | 68.02% | 94.99% | 64.45% | 95.38% | 81.61% | 647 | 141 |
| 3 | 79.57% | 61.75% | 60.09% | 68.67% | 81.10% | 446 | 1238 |
| 5 | 80.81% | 88.12% | 85.42% | 95.20% | 87.16% | 683 | 246 |
| 6 | 80.68% | 73.43% | 86.97% | 90.19% | 90.59% | 442 | 580 |

TABLE 6

| Donor | Accuracy | Precision | Recall | Average Precision | AUC | Activated Count | Quiescent Count |
|---|---|---|---|---|---|---|---|
| 1 | 88.13% | 55.35% | 50.64% | 53.67% | 79.92% | 235 | 1551 |
| 2 | 65.99% | 96.56% | 60.74% | 94.46% | 79.34% | 647 | 141 |
| 3 | 81.59% | 68.89% | 55.61% | 68.12% | 74.68% | 446 | 1238 |
| 5 | 80.92% | 89.32% | 84.11% | 95.20% | 86.68% | 683 | 246 |
| 6 | 83.02% | 78.17% | 84.49% | 89.86% | 89.02% | 442 | 580 |

TABLE 7

| Donor | Accuracy | Precision | Recall | Average Precision | AUC | Activated Count | Quiescent Count |
|---|---|---|---|---|---|---|---|
| 1 | 95.74% | 86.98% | 79.57% | 88.85% | 95.61% | 235 | 1551 |
| 2 | 76.65% | 91.56% | 78.83% | 95.24% | 82.33% | 647 | 141 |
| 3 | 92.16% | 94.60% | 74.66% | 93.07% | 96.26% | 446 | 1238 |
| 5 | 81.81% | 81.81% | 96.78% | 93.74% | 86.70% | 683 | 246 |
| 6 | 89.33% | 82.33% | 95.93% | 95.97% | 97.01% | 442 | 580 |

Non-linear models with image pixels as input have accuracies comparable to the logistic regression model with CellProfiler features. We tune the learning rate, batch size and the number of hidden layer neurons of the simple neural network with one hidden layer. Even though its average accuracy of 86.48% (FIG. 5 and Table 8) is slightly lower than logistic regression with CellProfiler features, it has more stable performance across the test donors. In comparison, the LeNet CNN has a more complex architecture and takes advantage of the image structure of the input data. After selecting the best learning rate and batch size, LeNet reaches an average accuracy of 89.51% (FIG. 5 and Table 9).

TABLE 8

| Donor | Accuracy | Precision | Recall | Average Precision | AUC | Activated Count | Quiescent Count |
|---|---|---|---|---|---|---|---|
| 1 | 88.80% | 55.28% | 75.74% | 65.40% | 90.55% | 235 | 1551 |
| 2 | 82.87% | 96.05% | 82.69% | 96.60% | 88.78% | 647 | 141 |
| 3 | 88.54% | 82.14% | 72.20% | 84.59% | 90.34% | 446 | 1238 |
| 5 | 84.78% | 85.58% | 95.19% | 96.48% | 92.05% | 683 | 246 |
| 6 | 87.41% | 80.62% | 93.48% | 94.44% | 95.36% | 442 | 580 |

TABLE 9

| Donor | Accuracy | Precision | Recall | Average Precision | AUC | Activated Count | Quiescent Count |
|---|---|---|---|---|---|---|---|
| 1 | 94.23% | 78.21% | 77.87% | 82.15% | 95.36% | 235 | 1551 |
| 2 | 87.06% | 96.58% | 87.33% | 97.86% | 91.92% | 647 | 141 |
| 3 | 91.45% | 95.76% | 70.85% | 91.55% | 94.12% | 446 | 1238 |
| 5 | 87.41% | 87.83% | 96.19% | 96.40% | 92.41% | 663 | 246 |
| 6 | 87.38% | 78.61% | 97.29% | 96.70% | 97.36% | 442 | 580 |

Our most advanced models using the pre-trained CNN outperform all other methods. Both versions of the pre-trained CNN use cell images as input and require a previously trained CNN. For one version, we use the pre-trained CNN as a feature extractor and then train a new hidden layer with off-the-shelf features. Alternatively, we fine-tune multiple higher-level layers of the CNN with T cell images. We include the fine-tuned layers as a hyper-parameter. Specifically, we define n, ranging from 1 to 11, as the number of last Inception modules in the pre-trained Inception v3 CNN to fine-tune. For example, if n=1, we only fine-tune the last Inception module, whereas we fine-tune all the layers of the Inception v3 CNN when n=11. After tuning n along with the other hyper-parameters, we compare the CNN with fine-tuning to the CNN off-the-shelf model in order to study the effect of fine-tuning on classifier performance. Additionally, we compare the test results of different n to analyze how the number of fine-tuned layers affects classification.

Figure 8:
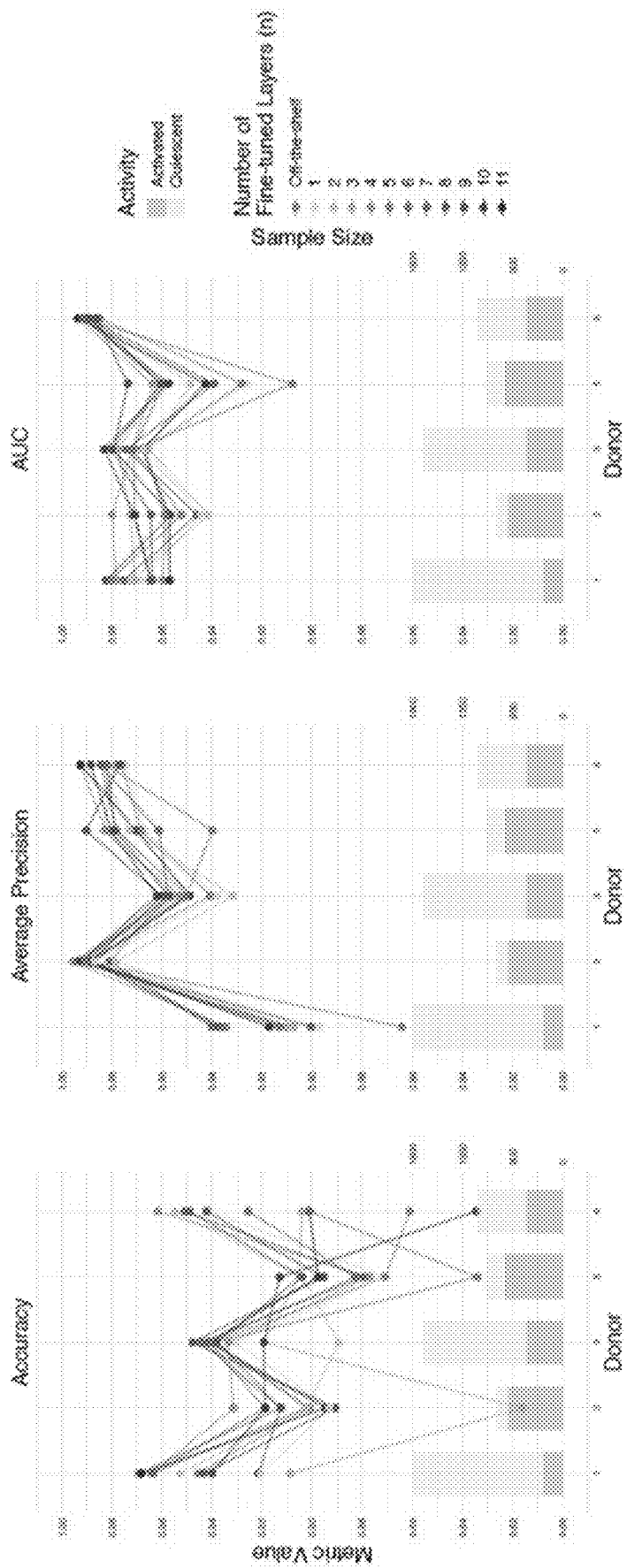
FIG. 8 is a performance comparison of fine-tuning a different number of layers and the pre-trained CNN off-the-shelf model, as described in Example 1.

The average accuracy for the pre-trained CNN off-the-shelf model is 90.36% (FIG. 5 and Table 10) and 93.56% for the pre-trained CNN with fine-tuning (FIG. 5 and Table 11). The fine-tuning model uses 11;10;7;11; and 8 layers as the optimal n for the five test donors. However, depending on the test donor and the evaluation metric, the number of fine-tuned layers does not necessarily have a strong effect on the predictive performance (FIG. 8). Different n values yield similar evaluation metrics. Fine-tuning all 11 layers also greatly increases the CNN training time (see, FIGS. S3 and S4 of Appendix A of U.S. Provisional Patent Application No. 62/886,139, which is incorporated herein in its entirety by reference).

TABLE 10

| Donor | Accuracy | Precision | Recall | Average Precision | AUC | Activated Count | Quiescent Count |
|---|---|---|---|---|---|---|---|
| 1 | 94.57% | 81.08% | 76.60% | 86.42% | 95.96% | 235 | 1551 |
| 2 | 90.10% | 96.87% | 90.88% | 99.06% | 95.89% | 647 | 141 |
| 3 | 93.94% | 93.22% | 83.18% | 94.08% | 96.66% | 446 | 1238 |
| 5 | 87.08% | 87.09% | 96.78% | 96.83% | 92.81% | 683 | 246 |
| 6 | 86.11% | 75.95% | 99.32% | 97.61% | 98.49% | 442 | 580 |

TABLE 11

| Donor | Accuracy | Precision | Recall | Average Precision | AUC | Activated Count | Quiescent Count |
|---|---|---|---|---|---|---|---|
| 1 | 96.81% | 92.79% | 82.13% | 91.71% | 95.70% | 235 | 1551 |
| 2 | 91.88% | 97.24% | 92.74% | 99.22% | 97.09% | 647 | 141 |
| 3 | 94.42% | 96.32% | 82.06% | 95.75% | 97.41% | 446 | 1238 |
| 5 | 89.77% | 89.20% | 97.95% | 97.02% | 94.26% | 683 | 246 |
| 6 | 94.91% | 92.76% | 95.70% | 98.20% | 98.91% | 442 | 580 |

Results: Confirming Generalization with a New Donor

In order to evaluate our ability to generalize to T cell images from a new individual, we completely hold out images from donor 4 during the study design, model implementation, and cross-validation above. We apply the same nested cross-validation scheme to train, tune, and test the pre-trained CNN with fine-tuning, the most accurate model in the previous cross-validation, on images from donor 4. It gives an accuracy of 98.83% (Table 12). Out of 2,051 predictions, there are only 4 false positives and 20 false negatives. The performance metrics in Table 12 are substantially higher than their counterparts in Table 11. Having training data from five donors instead of four likely contributes to the improved performance.

TABLE 12

| Donor | Accuracy | Precision | Recall | Average Precision | AUC | Activated Count | Quiescent Count |
| --- | --- | --- | --- | --- | --- | --- | --- |
| 4 | 98.83% | 99.14% | 95.85% | 99.79% | 99.93% | 482 | 1569 |

Results: Pre-Trained CNN with Fine-Tuning Errors

We inspect the T cell images that the pre-trained CNN with fine-tuning classifies incorrectly in order to better understand its failures and accuracy. We visualize the misclassified images for all test donors (see, FIGS. S5-S10 of Appendix A of U.S. Provisional Patent Application No. 62/886,139, which is incorporated herein in its entirety by reference) along with the predicted label, the Softmax score of the network output layer, and the temperature scaled confidence calibration. The majority of misclassified cell images are badly cropped, with no cells or multiple cells included in the frame. Therefore, using a more progressive dim image filter or adding a multiple-cell detector in the image processing pipeline could further improve the model performance. However, for other images with a clear single cell in the frame, the pre-trained CNN tends to give high confidence in its misclassification. These scores suggest that these errors cannot be easily fixed without a more powerful classifier or more diverse training dataset. Temperature scaling could either soften the original Softmax score toward 50% or increase the confidence toward 100%. For the misclassified images in our study, temperature scaling always drops the Softmax probability. This observation matches Guo et al.'s finding that neural networks with higher model capacity are more likely to be overconfident in their predictions.

Results: Pre-Trained CNN with Fine-Tuning Interpretation

Figure 9:
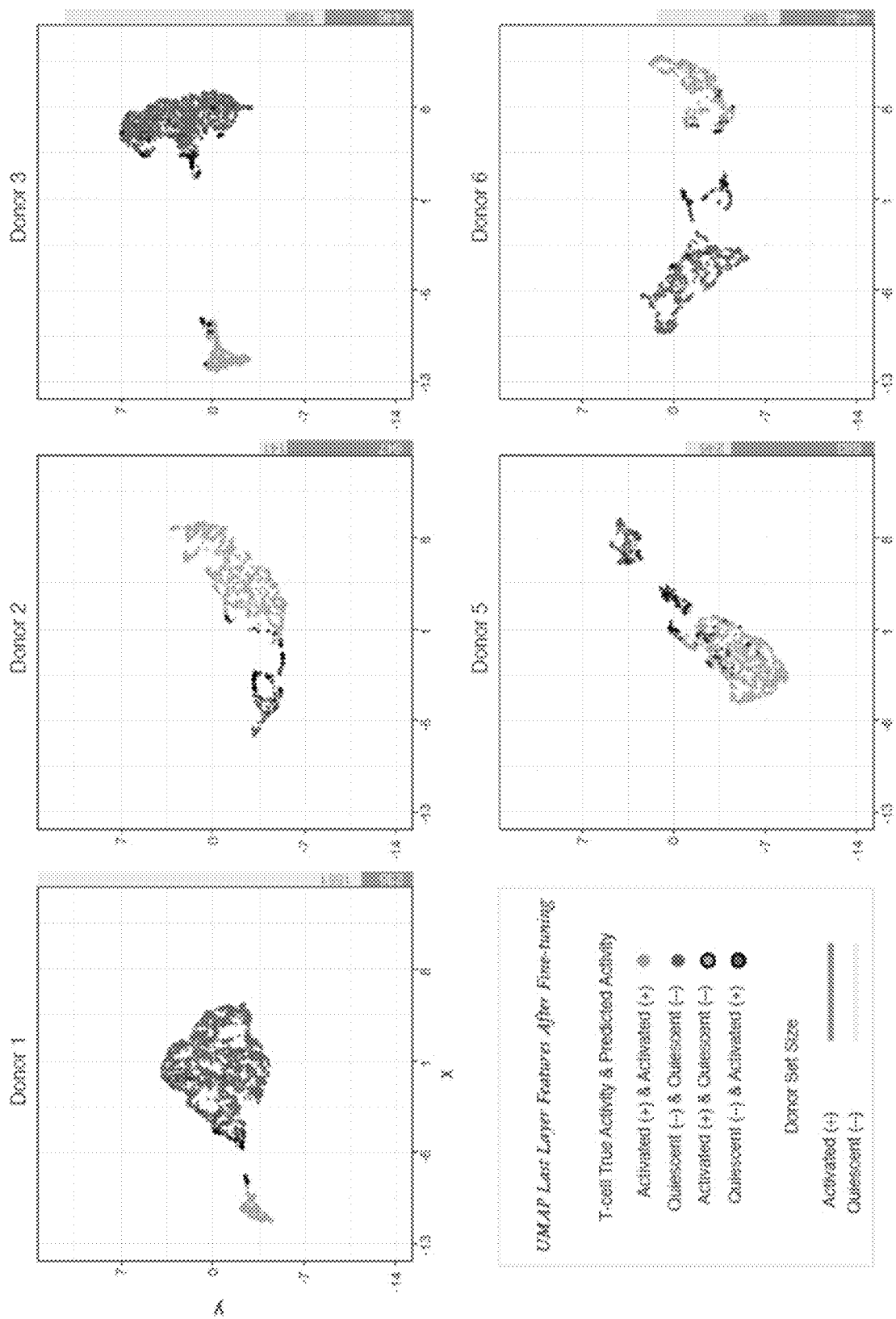
FIG. 9 includes 2D representations of T cell features extracted from the pre-trained CNN with fine-tuning, as described in Example 1. Dimensions are reduced from 2048 using UMAP. Data points with thick outlines indicate incorrect cell activity state predictions.

Visualizing the T cell dataset in 2D helps us understand why some classifiers perform better than others. We use Uniform Manifold Approximation and Projection (UMAP) to project the images into 2D such that similar images in the original feature space are nearby in the 2D space. Coloring the images with their activity labels shows how different input representations or learned representations separate the activated and quiescent cells. For example, in FIG. 9, each dot corresponds to one image based on its representation in the last layer of the pre-trained CNNs with fine-tuning. UMAP projects the 2048 learned features in the last layer of the CNN into 2D. In general, the activated and quiescent cells are well-separated in the 2D space, suggesting that the CNN has successfully learned distinct representations for the two types of T cells. Using t-Distributed Stochastic Neighbor Embedding (t-SNE) instead of UMAP for dimension reduction provides qualitatively similar results (see, FIG. S11 of Appendix A of U.S. Provisional Patent Application No. 62/886,139, which is incorporated herein in its entirety by reference).

Generating similar UMAP plots for three alternative image representations shows that the two image classes are not as well separated (see, FIGS. S12-S14 of Appendix A of U.S. Provisional Patent Application No. 62/886,139, which is incorporated herein in its entirety by reference). When using the raw pixel features (see, FIG. S12 of Appendix A of U.S. Provisional Patent Application No. 62/886,139, which is incorporated herein in its entirety by reference), the two types of T cells are spread throughout the 2D space. This contributes to the lower performance of the logistic regression and fully connected neural network models that operate directly on pixel intensity. Similarly, there is only moderate spatial separation when using the CellProfiler features (see, FIG. S13 of Appendix A of U.S. Provisional Patent Application No. 62/886,139, which is incorporated herein in its entirety by reference) or the last layer of the CNN before fine-tuning it to predict T cell activity (see, FIG. S14 of Appendix A of U.S. Provisional Patent Application No. 62/886,139, which is incorporated herein in its entirety by reference). These comparisons demonstrate the strong effect of fine-tuning the pre-trained CNN and also help explain the superior performance of pre-trained CNNs over the logistic regression model with CellProfiler features. In addition, by labeling misclassified images as outlined dots in FIG. 9, we see where the pre-trained CNN with fine-tuning makes errors. The incorrect predictions are predominantly distributed in the boundary between the two clusters.

Figure 10:
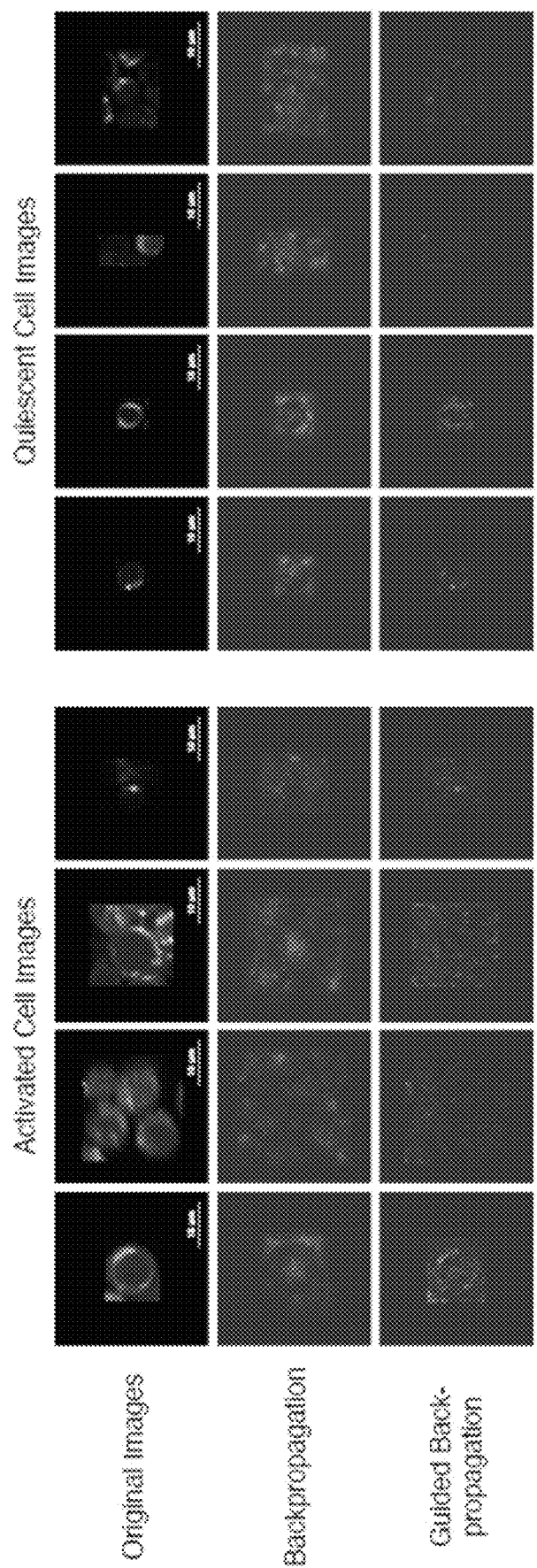
FIG. 10 shows saliency maps of randomly-selected cell images from donor 1 (scale bar: 10 µm), as described in Example 1. The backpropagation and guided backpropagation rows show two different techniques for generating saliency maps from the same T cell images in the first row.

In addition to visualizing the feature representation in the pre-trained CNNs with fine-tuning, we use saliency maps to interpret how these models make decisions. We generate saliency maps by computing the gradient of the CNN class score with respect to a few randomly chosen donor 1 images from both the activated and quiescent classes (FIG. 10). We use two methods to calculate gradients: standard backpropagation and guided backpropagation. In these heat maps, larger values (green or yellow) highlight the image regions that cause the most change in the T cell activity prediction. Smaller values (dark blue or purple) indicate pixels that have less influence. The uniformly dark blue background in both types of saliency maps indicates that the pre-trained CNNs with fine-tuning have learned to focus on the original cell image instead of the black padding. The larger values in the saliency maps with guided backpropagation often align with the high-intensity regions of the cell images, which correspond to mitochondria and depict metabolic activity. Although the influential regions of the guided backpropagation-based saliency maps are biologically plausible, this type of saliency map is insensitive to random changes of either the input data or model parameters. The saliency maps generated with standard backpropagation are properly affected by these randomized controls but do not concentrate on the high-intensity regions of the input images.

DISCUSSION

Our study demonstrates that machine learning models trained on autofluorescence intensity images can accurately classify activated and quiescent T cells across donors. Because autofluorescence images are easier to acquire with standard commercial microscopes compared to fluorescence lifetime images, this workflow has the potential to become a widely applicable approach for live T cell profiling. Fine-tuning a pre-trained CNN is the most powerful classification approach, outperforming alternative machine learning models that are commonly used for microscopy image classification over multiple evaluation metrics. In particular, this CNN applied directly to cropped images has better performance than logistic regression with domain-relevant features extracted by CellProfiler.

We thoroughly explored the effect of fine-tuning more layers of the pre-trained CNN and compared it with the off-the-shelf CNN model. The common transfer learning approach fixes the CNN parameters of the initial network layers, which extract learned features from the images, and trains a simple classifier from scratch that predicts the domain-specific image labels. Our results indicate that fine-tuning pre-trained CNN layers yields better performance than directly using off-the-shelf features. In addition, although fine-tuning more layers tends to give better predictive performance (FIG. 8), it is generally not worth the additional computational time and expense to fine-tune all 11 layers (see, FIGS. S3 and S4 of Appendix A of U.S. Provisional Patent Application No. 62/886,139, which is incorporated herein in its entirety by reference). Possible reasons include the limited sample size and relatively homogeneous cell image representations. Given the extra computational costs and implementation challenges, we recommend fine-tuning only the last few layers of a pre-trained CNN for similar autofluorescence microscopy applications. In settings that do require fine-tuning additional layers because the images are more heterogeneous, we suggest taking a larger step size in the layer number hyper-parameter optimization.

The machine learning models recognize image attributes that recapitulate biological domain knowledge. Activated T cells are larger in size. In addition, there are metabolic differences between quiescent and activated T cells, which are evident in the NAD(P)H images. The high intensity regions in the images likely correspond to mitochondria, where the majority of metabolism occurs. It is straightforward to inspect the trained logistic regression model that takes total image intensity and mask size as inputs and observe that it correctly recognizes the relationship between NAD(P)H intensity and activation state.

The parameters of the pre-trained CNN with fine-tuning are not as directly interpretable as the logistic regression model. An additional challenge is that different interpretation techniques provide distinct views of the fine-tuned CNN. Nevertheless, there are some indications in the saliency maps that this CNN also reflects T cell biology. Saliency maps help locate which regions of the input image influence the classification the most. With guided backpropagation, the high-intensity regions of the T cell images tend to be the focal points in the saliency maps. This suggests that the CNN may be sensitive to metabolic differences between quiescent and activated cells and not only changes in cell size. However, guided backpropagation and other more advanced saliency maps were found to be independent of the data, model, and model parameters. The standard backpropagation gradient map is sensitive to these controls, but it focuses more on general cell morphology than the metabolic activity within cells.

Each model in our study is only tuned and evaluated once, which limits our ability to assess the statistical significance of the performance differences across models. Substantial computing time and costs are required for nested cross-validation, especially when fine-tuning multiple layers of the pre-trained CNN (see, FIGS. S3 and S4 of Appendix A of U.S. Provisional Patent Application No. 62/886,139, which is incorporated herein in its entirety by reference). The fine-tuning jobs took 5,096 hours (212 days) in total to train on GPUs. Therefore, we are unable train each model multiple times to assess the variability in model performance due to random sampling, computer hardware, non-deterministic algorithms, and other factors. Slight differences in performance should not be over-interpreted.

Based on the misclassified images, the performance of the pre-trained CNN model with fine-tuning is limited by the image cropping quality. Some images contain multiple cells. Others do not contain any T cells. Developing a better filter to detect images with artifacts and adopting state-of-the-art segmentation approaches could further boost classification accuracy.

Overall, our strong results demonstrate the feasibility of classifying T cells directly from autofluorescence intensity images, which can guide future work to bring this technology to pre-clinical and clinical applications.

The present disclosure also includes the following statements:

1. A T cell classifying device comprising:
   a cell analysis pathway comprising:
   (i) an inlet;
   (ii) an observation zone coupled to the inlet downstream of the inlet, the observation zone configured to present T cells for individual autofluorescence interrogation; and
   (iii) an outlet coupled to the observation zone downstream of the observation zone;
   a single-cell autofluorescence image sensor configured to acquire an autofluorescence intensity image of a T cell positioned in the observation zone;
   a processor in electronic communication with the single-cell autofluorescence image sensor; and
   a non-transitory computer-readable medium accessible to the processor and having stored thereon a trained convolutional neural network and instructions that, when executed by the processor, cause the processor to:
   a) receive the autofluorescence intensity image;
   b) optionally pre-process the autofluorescence intensity image to produce an adjusted autofluorescence intensity image;
   c) input the autofluorescence intensity image or the adjusted autofluorescence intensity image into the trained convolutional neural network to produce an activation prediction for the T cell.

2. The T cell classifying device of statement 1, wherein the cell analysis pathway comprises a microfluidic pathway or a nanofluidic pathway.

3. The T cell classifying device of statement 1 or 2, the T cell classifying device further comprising a flow regulator coupled to the inlet.

4. The T cell classifying device of any one of the preceding statements, wherein the flow regulator is configured to provide flow of cells through the observation zone at a rate that allows the single-cell autofluorescence imager to acquire the autofluorescence image for the T cell when it is positioned in the observation zone.

5. The T cell classifying device of any one of the preceding statements, the T cell classifying device further comprising a light source.

6. The T cell classifying device of any one of the preceding statements, wherein the light source is a continuous wave light source.

7. The T cell classifying device of any one of the preceding statements, wherein the light source emits light having a wavelength tuned to excite fluorescence from NAD(P)H and/or FAD.

8. The T cell classifying device of any one of the preceding statements, wherein the single-cell autofluorescence image sensor is configured to acquire the autofluorescence intensity image at a repetition rate of between 1 kHz and 20 GHz.

9. The T cell classifying device of any one of the preceding statements, wherein the single-cell autofluorescence image sensor is configured to acquire the autofluorescence intensity image at a repetition rate of between 1 MHz and 1 GHz.

10. The T cell classifying device of any one of the preceding statements, wherein the single-cell autofluorescence image sensor is configured to acquire the autofluorescence intensity image at a repetition rate of 20 MHz and 100 MHz.

11. The T cell classifying device of any one of the preceding statements, wherein the single-cell autofluorescence image sensor is configured to acquire the autofluorescence intensity image via pixel-by-pixel intensity measurements.

12. The T cell classifying device of any one of the preceding statements, wherein the single-cell autofluorescence image sensor is a charge collection device array.

13. The T cell classifying device of any one of the preceding statements, the single-cell autofluorescence image sensor comprising a detector-side filter configured to transmit fluorescence signals of interest.

14. The T cell classifying device of the immediately preceding statement, wherein the detector-side filter is configured to transmit NAD(P)H fluorescence and/or FAD fluorescence.

15. The T cell classifying device of any one of the preceding statements, the T cell classifying device further comprising a cell size measurement tool configured to measure cell size and to communicate the cell size to the processor.

16. The T cell classifying device of any one of the preceding statements, the T cell classifying device further comprising a cell imager configured to acquire an image of a cell positioned within the observation zone and to communicate the image to the processor.

17. The T cell classifying device of any one of the preceding statements, wherein the instructions, when executed by the processor, cause the processor to: b) pre-process the autofluorescence intensity image to produce an adjusted autofluorescence intensity image; and c) input the adjusted autofluorescence intensity image into the trained convolutional neural network to produce the activation prediction for the T cell.

18. The T cell classifying device of the immediately preceding statement, wherein the pre-processing of step b) includes cropping the autofluorescence intensity image, padding the autofluorescence intensity image, rotating the autofluorescence intensity image, reflecting the autofluorescence intensity image, or a combination thereof.

19. The T cell classifying device of any one of the preceding statements, wherein the instructions, when executed by the processor, cause the processor to determine if the autofluorescence intensity image is an outlier and to skip steps b), c) and d) if the autofluorescence intensity image is an outlier.

20. The T cell classifying device of any one of the preceding statements, wherein the cell analysis pathway does not include a fluorescent label for binding to the T cell.

21. The T cell classifying device of any one of the preceding statements, wherein the autofluorescence image sensor is adapted to measure autofluorescence of T cells without requiring the use of a fluorescent label.

22. The T cell classifying device of any one of the preceding statements, wherein the cell analysis pathway does not include an immobilization agent for binding and immobilizing T cells.

23. The T cell classification device of any one of the preceding statements, the T cell classification device further comprising a cell sorter having a sorter inlet and at least two sorter outlets, the cell sorter coupled to the cell analysis pathway via the outlet downstream of the observation zone, the cell sorter configured to selectively direct a cell from the sorter inlet to one of the at least two sorter outlets based on a sort signal, the processor in electronic communication with the cell sorter, and the instructions, when executed by the processor, further cause the processor to provide the sort signal to the cell sorter based on the activation prediction.

24. The T cell classifying device of the immediately preceding statement, wherein the trained convolutional neural network, the processor, and physical dimensions and flow rate of the cell analysis pathway are adapted to provide the sorter signal to the cell sorter prior to the T cell reaching the cell sorter.

25. The T cell classifying device of any one of the preceding claims, wherein the instructions, when executed by the processor, further cause the processor to generate a report including the activation prediction for T cells having passed through the cell analysis pathway.

26. A method of characterizing T cell activation state, the method comprising:
   a) optionally receiving a population of T cells having unknown activation status;
   b) acquiring an autofluorescence intensity image for a T cell of the population of T cells;
   c) optionally pre-processing the autofluorescence intensity image to provide an adjusted autofluorescence intensity image; and
   d) identifying an activation status of the T cell based on an activation prediction, wherein the activation prediction is computed using the autofluorescence intensity image or the adjusted autofluorescence intensity image as an input for a trained convolutional neural network.

27. A method of classifying T cells, the method comprising:
   a) receiving a population of T cells having unknown activation status;
   b) acquiring an autofluorescence intensity image for each T cell of the population of T cells, thereby resulting in a set of autofluorescence intensity images;
   c) optionally pre-processing the autofluorescence intensity images of the set of autofluorescence intensity images to provide a set of adjusted autofluorescence intensity images; and
   either:
   d1) physically isolating a first portion of the population of T cells from a second portion of the population of T cells based on an activation prediction, wherein each T cell of the population of T cells is placed into the first portion when the activation prediction exceeds a predetermined threshold and into the second portion when the activation prediction is less than or equal to the predetermined threshold; or
   d2) generating a report including the activation prediction, the report optionally identifying a proportion of the population of T cells having the activation prediction that exceeds the predetermined threshold,
   wherein the activation prediction is computed using the autofluorescence intensity image from the set of autofluorescence intensity images or the adjusted autofluorescence intensity image from the set of adjusted autofluorescence intensity images corresponding to a given T cell as an input for a trained convolutional neural network.

28. The T cell classifying device or the method of any one of the preceding statements, wherein the autofluorescence intensity image is tuned to a wavelength corresponding to NAD(P)H fluorescence and/or FAD fluorescence.

29. The T cell classifying device or the method of any one of the preceding statements, wherein at least a portion of the trained convolutional neural network is initially pre-trained using images that are not fluorescence images of cells.

30. The T cell classifying device or the method of any one of the preceding statements, wherein at least a portion of the trained convolutional neural network includes an image classification network at least partially pre-trained using optical images of objects that are visible to the naked human eye.

31. The T cell classifying device or the method of any one of the preceding statements, wherein the trained convolutional neural network utilizes a spatial distribution of fluorescence intensity in producing the activation prediction.

32. The T cell classifying device or the method of any one of the preceding statements, wherein the trained convolutional neural network is trained using only fluorescence intensity images as an input.

33. The T cell classifying device or the method of any one of the preceding statements, wherein the trained convolutional neural network is not pre-trained or trained with a cell size attribute as an input and does not use the cell size attribute as an input to produce the activation prediction.

34. The T cell classifying device or the method of any one of the preceding statements, wherein the trained convolutional neural network is not pre-trained or trained with cell morphological features as an input and does not use cell morphological features as an input to produce the activation prediction.

35. The T cell classifying device or the method of any one of the preceding statements, wherein the trained convolutional neural network is trained on at least 100 images, at least 500 images, at least 1000 images, at least 2500 images, or at least 5000 images of T cells having known activation states.

36. The T cell classifying device or the method of any one of the preceding statements, wherein the trained convolutional neural network segments the autofluorescence intensity image.

37. The T cell classifying device or the method of any one of the preceding statements, wherein the trained convolutional neural network is instrument-specific.

38. The T cell classifying device or the method of any one of the preceding statements, wherein the trained convolutional neural network is patient-specific.

39. The T cell classifying device or the method of any one of the preceding statements, wherein the trained convolutional neural network provides a classification accuracy of at least 85%, at least 87.5%, at least 90%, at least 92.5%, at least 95%, at least 96%, at least 97%, or at least 98%.

40. The T cell classifying device or the method of any one of the preceding statements, wherein the trained convolutional neural network includes at least 5 layers, at least 6 layers, at least 7 layers, at least 8 layers, at least 9 layers, or at least 10 layers, and at most 100 layers, at most 50 layers, at most 20 layers, at most 17 layers, at most 15 layers, at most 14 layers, at most 13 layers, or at most 12 layers.

41. The T cell classifying device or the method of any one of the preceding statements, wherein the T cells whose activation prediction is positive are CD3+, CD4+ or CD8+ T cells.

42. The method of any one of statements 26 to the immediately preceding statement, wherein step c) is not optional and the activation prediction of step d) is computed using the adjusted autofluorescence intensity image.

43. The method of the immediately preceding claim, wherein the pre-processing of step c) includes cropping the autofluorescence intensity image, padding the autofluorescence intensity image, rotating the autofluorescence intensity image, reflecting the autofluorescence intensity image, or a combination thereof.

44. The method of any one of statements 26 to the immediately preceding statement, the method further comprising determining if the autofluorescence intensity image is an outlier and skipping step d) if the autofluorescence intensity image is an outlier.

45. The method of any one of statements 26 to the immediately preceding statement, wherein the method does not involve use of a fluorescent label for binding to the T cell.

46. The method of any one of statements 26 to the immediately preceding statement, wherein the method does not involve immobilizing the T cell.

47. A method of administering activated T cells to a subject in need thereof, the method comprising:
 a) the method of any one of statements 27 to the immediately preceding statement, wherein the method comprises step d1); and
 b) introducing the first portion of the population of T cells to the subject.

48. The method of statement 47, wherein the first portion of the population of T cells is modified prior to step b).

49. The method of statement 48, wherein the first portion of the population of T cells is modified to include a chimeric antigen receptor prior to step b).

50. A method of administering activated T cells to a subject in need thereof, the method comprising:
 a) the method of any one of statements 27 to 46, wherein the method comprises step d2); and
 b) in response to the proportion exceeding a second predetermined threshold, introducing the population of T cells to the subject.

51. The method of the immediately preceding statement, wherein the population of T cells is modified prior to step b).

52. The method of the immediately preceding statement, wherein the population of T cells is modified to include a chimeric antigen receptor prior to step b).

We claim:

1. A T cell classifying device comprising:
 a cell analysis pathway comprising:
 (i) an inlet;
 (ii) an observation zone coupled to the inlet downstream of the inlet, the observation zone configured to present T cells for individual autofluorescence interrogation; and
 (iii) an outlet coupled to the observation zone downstream of the observation zone;
 a single-cell autofluorescence image sensor configured to acquire an autofluorescence intensity image of a T cell positioned in the observation zone;
 a processor in electronic communication with the single-cell autofluorescence image sensor; and
 a non-transitory computer-readable medium accessible to the processor and having stored thereon a trained convolutional neural network and instructions that, when executed by the processor, cause the processor to:
 a) receive the autofluorescence intensity image;
 b) optionally pre-process the autofluorescence intensity image to produce an adjusted autofluorescence intensity image;
 c) input the autofluorescence intensity image or the adjusted autofluorescence intensity image into the trained convolutional neural network to produce an activation prediction for the T cell.

2. The T cell classifying device of claim 1, wherein the autofluorescence intensity image is tuned to a wavelength corresponding to NAD(P)H fluorescence and/or FAD fluorescence.

3. The T cell classifying device of claim 1, wherein at least a portion of the trained convolutional neural network is initially pre-trained using images that are not fluorescence images of cells.

4. The T cell classifying device of claim 1, wherein at least a portion of the trained convolutional neural network includes an image classification network at least partially pre-trained using optical images of objects that are visible to the naked human eye.

5. The T cell classifying device of claim 1, wherein the trained convolutional neural network utilizes a spatial distribution of fluorescence intensity in producing the activation prediction.

6. The T cell classifying device of claim 1, wherein the trained convolutional neural network is trained using only fluorescence intensity images as an input.

7. The T cell classifying device of claim 1, wherein the trained convolutional neural network is not pre-trained or trained with a cell size attribute as an input and does not use the cell size attribute as an input to produce the activation prediction.

8. The T cell classifying device of claim 1, wherein the trained convolutional neural network is not pre-trained or trained with cell morphological features as an input and does not use cell morphological features as an input to produce the activation prediction.

9. The T cell classifying device of claim 1, wherein the trained convolutional neural network segments the autofluorescence intensity image.

10. The T cell classifying device of claim 1, wherein the trained convolutional neural network provides a classification accuracy of at least 85%.

11. The T cell classifying device of claim 1, wherein the instructions, when executed by the processor, cause the processor to: b) pre-process the autofluorescence intensity image to produce an adjusted autofluorescence intensity image; and c) input the adjusted autofluorescence intensity image into the trained convolutional neural network to produce the activation prediction for the T cell.

12. The T cell classifying device of claim 11, wherein the pre-processing of step b) includes cropping the autofluorescence intensity image, padding the autofluorescence intensity image, rotating the autofluorescence intensity image, reflecting the autofluorescence intensity image, or a combination thereof.

13. The T cell classifying device of claim 1, wherein the instructions, when executed by the processor, cause the processor to determine if the autofluorescence intensity image is an outlier and to skip steps b), c) and d) if the autofluorescence intensity image is an outlier.

14. A method of classifying T cells, the method comprising:
a) receiving a population of T cells having unknown activation status;
b) acquiring an autofluorescence intensity image for each T cell of the population of T cells, thereby resulting in a set of autofluorescence intensity images;
c) optionally pre-processing the autofluorescence intensity images of the set of autofluorescence intensity images to provide a set of adjusted autofluorescence intensity images; and
either:
d1) physically isolating a first portion of the population of T cells from a second portion of the population of T cells based on an activation prediction, wherein each T cell of the population of T cells is placed into the first portion when the activation prediction exceeds a predetermined threshold and into the second portion when the activation prediction is less than or equal to the predetermined threshold; or
d2) generating a report including the activation prediction, the report optionally identifying a proportion of the population of T cells having the activation prediction that exceeds the predetermined threshold,
wherein the activation prediction is computed using the autofluorescence intensity image from the set of autofluorescence intensity images or the adjusted autofluorescence intensity image from the set of adjusted autofluorescence intensity images corresponding to a given T cell as an input for a trained convolutional neural network.

15. The method of claim 14, wherein step c) is performed and the activation prediction of step d1) or step d2) is computed using the adjusted autofluorescence intensity image.

16. The method of claim 15, wherein the pre-processing of step c) includes cropping the autofluorescence intensity image, padding the autofluorescence intensity image, rotating the autofluorescence intensity image, reflecting the autofluorescence intensity image, or a combination thereof.

17. The method of claim 14, the method further comprising determining if the autofluorescence intensity image is an outlier and skipping both step d1) and step d2) if the autofluorescence intensity image is an outlier.

18. The method of claim 14, wherein the autofluorescence intensity image is tuned to a wavelength corresponding to NAD(P)H fluorescence and/or FAD fluorescence.

19. The method of claim 14, wherein at least a portion of the trained convolutional neural network is initially pre-trained using images that are not fluorescence images of cells.

20. A method of administering activated T cells to a subject in need thereof, the method comprising:
the method of claim 14; and
introducing the first portion of the population of T cells to the subject.

* * * * *